(12) United States Patent
Bulich et al.

(10) Patent No.: US 11,562,812 B2
(45) Date of Patent: Jan. 24, 2023

(54) COMPUTER IMPLEMENTED METHOD FOR SECURE MANAGEMENT OF DATA GENERATED IN AN EHR DURING AN EPISODE OF CARE AND A SYSTEM THEREFOR

(71) Applicant: E-NOME PTY LTD, Elizabeth Bay (AU)

(72) Inventors: John Bulich, City Beach (AU); Nuno Cristina Martins, City Beach (AU); Govert Van Ek, City Beach (AU); Oliver Peter Curtis, Vaucluse (AU); Nicholas Anthony Curtis, Elizabeth Bay (AU)

(73) Assignee: E-NOME PTY LTD

( * ) Notice: Subject to any disclaimer, the term of this patent is extended or adjusted under 35 U.S.C. 154(b) by 868 days.

(21) Appl. No.: 16/317,970

(22) PCT Filed: Jul. 14, 2017

(86) PCT No.: PCT/AU2017/050729
§ 371 (c)(1),
(2) Date: Jan. 15, 2019

(87) PCT Pub. No.: WO2018/009979
PCT Pub. Date: Jan. 18, 2018

(65) Prior Publication Data
US 2021/0295961 A1     Sep. 23, 2021

(30) Foreign Application Priority Data

Jul. 15, 2016  (AU) .............................. 2016902791
Jul. 14, 2017  (WO) ............... PCT/AU2017/050729

(51) Int. Cl.
G16H 10/60      (2018.01)
G06F 21/62      (2013.01)
(Continued)

(52) U.S. Cl.
CPC .......... *G16H 10/60* (2018.01); *G06F 16/245* (2019.01); *G06F 16/27* (2019.01);
(Continued)

(58) Field of Classification Search
CPC combination set(s) only.
See application file for complete search history.

(56) References Cited

U.S. PATENT DOCUMENTS 9,849,364 B2 * 12/2017 Tran .................... A63B 60/16
10,231,077 B2 *  3/2019 Raduchel ............... G16H 10/65
(Continued)

FOREIGN PATENT DOCUMENTS

| WO | 2001/018631 A1 | 3/2001 |
| WO | 2001/046826 A1 | 6/2001 |
| WO | 2005/109292 A2 | 11/2005 |

*Primary Examiner* — Hosuk Song
(74) *Attorney, Agent, or Firm* — Thorpe North & Western, LLP

(57) ABSTRACT

There is provided a computer implemented method for secure management of data generated in an Electronic Health Record (EHR) during an episode of care, for a user, wherein the EHR is being maintained in a medical database (140) comprised within a Healthcare Service Provider (HSP) server (130), the computer implemented method comprising the steps of sending an identification hash corresponding to the user to an Application Program Interface (API) server (150) from a first client device (110a); extracting the data from the HSP server (130) and de-identifying the data to obtain de-identified data at the API server (150); generating a record hash at the API server (150); transmitting the identification hash, the record hash and the de-identified data from the API server (150) to a core server (160); receiving the identification hash, the record hash and the de-identified data at the core server (160) and transmitting the identification hash, the record hash and the de-identified data from the core server (160) to a repository database (170) to
(Continued)

generate a record identification; transmitting the de-identified data, the record hash and the record identification from the repository database (170) to the first client device (110*a*), via the core server (160); generating a data hash by hashing the de-identified data and a plurality of attributes corresponding to the de-identified data; generating at the core server (160) a register package based on the data hash, the identification hash and the record hash; storing the register package, from the core server (160), on to a blockchain (180) to generate a transaction identification; transmitting the data hash and the transaction identification from the core server (160) to the repository database (170); and transmitting the transaction identification and the data hash from the repository database (170) to the first client device (110*a*), via the core server (160).

58 Claims, 14 Drawing Sheets

(51) Int. Cl.
*H04L 9/30* (2006.01)
*H04L 9/32* (2006.01)
*H04L 9/00* (2022.01)
*G06F 16/27* (2019.01)
*G06F 16/245* (2019.01)
*H04L 9/06* (2006.01)

(52) U.S. Cl.
CPC ........ *G06F 21/6254* (2013.01); *H04L 9/0643* (2013.01); *H04L 9/30* (2013.01); *H04L 9/3239* (2013.01); *H04L 9/50* (2022.05)

(56) References Cited

U.S. PATENT DOCUMENTS

| | | | | |
|---|---|---|---|---|
| 10,484,178 | B2* | 11/2019 | Andrade | H04L 63/0861 |
| 10,789,590 | B2* | 9/2020 | Tran | H04L 9/3236 |
| 11,063,770 | B1* | 7/2021 | Peng | G06F 21/6227 |
| 11,153,069 | B2* | 10/2021 | Kurian | H04L 9/3239 |
| 2001/0018739 | A1* | 8/2001 | Anderson | G06Q 10/10 |
| | | | | 380/243 |
| 2008/0147554 | A1 | 6/2008 | Stevens et al. | |
| 2012/0078663 | A1 | 3/2012 | Lorsch | |
| 2012/0226916 | A1 | 9/2012 | Hahn et al. | |
| 2015/0149208 | A1 | 5/2015 | Lynch et al. | |
| 2016/0034713 | A1 | 2/2016 | Ramirez | |
| 2016/0110505 | A1 | 4/2016 | Symanski et al. | |
| 2016/0275309 | A1 | 9/2016 | Austin et al. | |
| 2017/0132625 | A1* | 5/2017 | Kennedy | G06F 16/2379 |

* cited by examiner

COMPUTER IMPLEMENTED METHOD FOR SECURE MANAGEMENT OF DATA GENERATED IN AN EHR DURING AN EPISODE OF CARE AND A SYSTEM THEREFOR

FIELD OF THE INVENTION

The present invention relates to Electronic Health Records (EHR) and in particular to a system and a method for secure management of data generated in an EHR during an episode of care.

The invention has been developed primarily for use in/with EHRs and will be described hereinafter with reference to this application. However, it will be appreciated that the invention is not limited to this particular field of use.

BACKGROUND OF THE INVENTION

An Electronic Health Record (EHR) is a digitized form of a user's medical history. The EHR may contain information such as physical characteristics of the user, history of diseases, immunization history and radiological reports etc. Additionally, the EHR may contain other important data such as duration of an illness, geographical location and time of an episode of care. The EHR may be created in a medical database provided with a Healthcare Service Provider (HSP) in a multitude of different formats. Some of the commonly accepted formats currently available in the domain include FHIR and HL7.

However, where EHRs are being increasingly accepted by HSPs including individual clinicians and hospitals as an effective way of managing user related data, there is a lack of a single universally accepted standard for creating such records. Different HSPs may opt for maintaining EHRs in different formats. This makes it difficult for the user seeking services from more than one HSP, as it would be difficult to combine medical records generated during individual episodes of care, because of a lack of compatibility between individual EHR formats. Even, in a case where the individual EHR formats are compatible, it adds an additional workflow for the HSP to upload the data to a central database. Significant advances have been made, for example through the adoption of LOINC codes and the SNOMED system, but regional variations are still a significant problem.

There have been a number of solutions offered to the above mentioned problems, some of which have been discussed below:

US20160110505A1 provides a system for storage and management of EHRs in a plurality of formats. Each EHR from the plurality of EHRs is created with a corresponding ontology and stored in a database along with details of the ontology. When an EHR from the plurality of EHRs, is requested by an HSP, the EHR may be provided to the HSP directly or may be translated to have a different ontology before providing the EHR to the HSP.

US20120078663A1 discloses a system for accepting a patient's record in one format and convert it into a second desirable format. The patient's record may include practice management data, electronic health records and personal health records etc.

While the aforementioned documents and other solutions in the art strive to provide methods and systems for secure management of data generated during an episode of care in an EHR, they still suffer from a plurality of discrepancies. First, the existing systems, also store identification details of the user. The identification details are either stored directly in association with the data, in a database, or stored at a different location and combined with the data while transmittal of the data to a user device. The storing of identification details creates a serious security risk in an event of a system being hacked. Further, the data is also at risk during transmittal of the data from the database to the user device, or during the transmittal of data from the HSP to the database. So in case where the database may adopt stringent security measures to prevent theft of the identification details during hacking attacks, the identification details of the user may be stolen during transmission through attacks such as Man in the Middle (MITM) attacks.

Moreover, the existing systems do not provide enough safeguards for preventing the data from being tampered with, by the user. The user may alter specific details in the data for making false insurance claims or for other malicious purposes. Recent trends have depicted insurance services providers suffering serious losses due to false insurance claims.

Therefore there remains, in the art, a need for improved systems and methods for secure management of data generated in an EHR during an episode of care which prevents the identification details of the user from being stolen and also provides sufficient safeguards for preventing the data from being tampered with.

Any discussion of the background art throughout the specification should in no way be considered as an admission that such background art is prior art, nor that such background art is widely known or forms part of the common general knowledge in the field in Australia or any other country.

SUMMARY OF THE INVENTION

According to a first aspect of the invention, there is provided a computer implemented method for secure management of data generated in an Electronic Health Record (EHR) during an episode of care, for a user, wherein the EHR is being maintained in a medical database comprised within a Healthcare Service Provider (HSP) server, the computer implemented method comprising the steps of sending an identification hash corresponding to the user to an Application Program Interface (API) server from a first client device, extracting the data from the HSP server and de-identifying the data to obtain de-identified data at the API server, generating a record hash at the API server, transmitting the identification hash, the record hash and the de-identified data from the API server to a core server, receiving the identification hash, the record hash and the de-identified data at the core server and transmitting the identification hash, the record hash and the de-identified data from the core server to a repository database to generate a record identification, transmitting the de-identified data, the record hash and the record identification from the repository database to the first client device, via the core server, generating a data hash by hashing the de-identified data and a plurality of attributes corresponding to the de-identified data and generate a register package at the core server based on the data hash, the identification hash and the record hash, storing the register package, from the core server, on to a blockchain to generate a transaction identification, transmitting the data hash and the transaction identification from the core server to the repository database and transmitting the transaction identification and the data hash from the repository database to the first client device, via the core server.

The computer implemented methods described above offer a plurality of advantages over existing system and methods. Specifically, the identification details of the user are not stored on either of the core server and/or the repository database. Therefore, in a scenario, where the core server and/or the repository database are hacked, there will be no way of linking the de-identified data back to the user. Further, because EHR details can be verified using the register package on the blockchain, no trusted centralized register of the user needs to exist. Furthermore, Storing of the register package onto the blockchain ensures that no reverse lookup table is required to link the data with an identity of the user.

In one embodiment of the invention, the computer implemented method further comprises the steps of generating an asymmetrical pair of a public key and a private key at the first client device, concatenating a first nonce to the public key to obtain a first resultant string, and applying a hashing algorithm to the first resultant string to obtain a user hash, at the first client device, generating a second nonce corresponding to the user hash, at the core server, transmitting the second nonce to the first client device from the core server and concatenating the second nonce to the user hash to obtain a second resultant string, and applying the hashing algorithm to the second resultant string to obtain the identification hash, at the first client device. The use of first nonce protects the public key, whereas the second nonce protects the user hash.

In one embodiment of the invention, the identification hash is send to the API server through a first offline communication medium. The use of offline communication medium ensures that identity of the first client device or the user is not exposed for interception.

In one embodiment of the invention, the first offline communication medium is selected from a group including Quick Response (QR) code, Near Field Communication (NFC) and Bluetooth.

In one embodiment of the invention, the computer implemented method further comprises the steps of displaying one or more first details corresponding to the user on the first client device to allow verification of an identity of the user.

In one embodiment of the invention, the plurality of attributes comprise a geographical location tag and a time stamp. The use of geographical location tag and the time stamp for generating data ensures that the time and location of the episode of care cannot be tampered with.

In one embodiment of the invention, the de-identified data, the record identification, the transaction identification, the record hash and the data hash is transmitted to the first client device in response to receiving of the identification hash from the first client device. The identification hash is the only parameter linking the de-identified data to the first client device. Hence, the identity of the first client device is not disclosed anywhere in the system.

In one embodiment of the invention, the computer implemented method further comprises the steps of regenerating the register package based on the identification hash, the record hash and the data hash at the first client device and verifying the register package with the blockchain, by using the transaction identification, from the first client device. The first client device can verify the register package at any time using the transaction identification.

In one embodiment of the invention, the computer implemented method further comprises the step of verifying the de-identified data with the first client device, after transmitting the de-identified data to the first client device from the core server. This step allows for the de-identified data to be verified by the user, before storing of de-identified data in the repository database In one embodiment of the invention, the computer implemented method further comprises the step of verifying the register package with the first client device before storing the register package onto the blockchain. This step allows for the register package to be verified by the first client device, before storing the register package onto the blockchain. Only the first client device can verify the register package using the private key.

In one embodiment of the invention, the computer implemented method further comprising the steps of regenerating the register package at the first client device based on the identification hash, the record hash and the data hash, sending the record identification and a portion of the register package to a second client device, from the first client device, sending the record identification and the portion of the register package to the core server for retrieval of the de-identified data, from the second client device, querying the repository database from the core server using the record identification and the portion of the register package and receiving the transaction identification, the identification hash, the record hash, the data hash and the de-identified data at the core server from the repository database in response to the query and sending, from the core server, at least one of the de-identified data and a first viewing medium to the second client device, the first viewing medium being configured for viewing of the de-identified data at the second client device. The first viewing medium may be provided in cases where the de-identified data is too large to be transmitted.

In one embodiment of the invention, the computer implemented method further comprises the steps of regenerating the register package at the core server based on the identification hash, the record hash and the data, sending the register package and the transaction identification from the core server to the second client device and verifying the register package with the blockchain using the transaction identification, from the second client device.

In one embodiment of the invention, the computer implemented method further comprises the steps of regenerating the register package at the core server based on the identification hash, the record hash and the data hash and verifying the regenerated register package with the portion of the register package received from the second client device, at the core server.

In one embodiment of the invention, the record identification and the portion of the register package are sent to the second client device through a second offline communication medium. The use of offline communication medium ensures that identity of the first client device or the user is not exposed for interception.

In one embodiment of the invention, the second offline communication medium is selected from a group including Quick Response (QR) code, Near Field Communication (NFC) and Bluetooth.

In one embodiment of the invention, the computer implemented method further comprises the step of sending one or more second details corresponding to the user by the first client device for verification of an identity of the user.

In one embodiment of the invention, the computer implemented method further comprises the steps of regenerate the register package at the first client device based on the identification hash, the record hash and the data hash, sending the register package and the transaction identification to a claims authorization server, from the first client device, verifying the register package with the blockchain from the claims authorization server, using the transaction identification and returning a confidence value from the claims authorization server to the first client device on verification of the register package. This is to ensure that the plurality of attributes such as the time stamp and the geographical location tag of the episode of care have not been tampered with. Any modification to any of the plurality of attributes will lead to generation of an erroneous register package In one embodiment of the invention, the computer implemented method further comprises the steps of generating a research query at a third client device, the research query comprising a plurality of characteristics, sending the research query to the core server from the third client device, verifying from the core server, of a presence of at least one characteristic from the plurality of characteristics, in the de-identified data stored at the repository database, requesting the first client device for an access to the de-identified data from the core server, on verification of the presence of the at least one characteristic, receiving the record identification from the first client device in response to the request, at the core server and transmitting the record identification to a research database, from the core server, generating a research record hash at the core server, and transmitting the research record hash to the research database to be stored in association with the record identification and transmitting the research record hash to the third client device.

In one embodiment of the invention, the computer implemented method further comprises the steps of querying the core server using the research record hash for viewing of the de-identified data, from the third client device, querying the research database from the core server using the research record hash and receiving the record identification at the core server from the research database, querying the repository database from the core server using the record identification and receiving the de-identified data at the core server from the repository database, sending, from the core server, a second viewing medium to the third client device, the second viewing medium being configured for viewing of the de-identified data at the third client device. The research query can be used to conduct disease related research, study epidemiological patterns and conduct surveys. Further, only the second viewing medium, such as a link, is sent to the third client device. The link may be temporary. Hence confidentiality of the de-identified data is maintained.

In one embodiment of the invention, the first client device receives the request for access to the de-identified data on sending the identification hash to the core server.

According to a second aspect of the invention, there is provided a computer implemented method for secure management of data generated in an Electronic Health Record (EHR) during an episode of care, for a user, wherein the EHR is being maintained in a medical database comprised within a Healthcare Service Provider (HSP) server. The computer implemented method comprises the steps of sending an identification hash corresponding to the user to an Application Program Interface (API) server from a first client device, extracting the data from the HSP server and de-identifying the data to obtain de-identified data, at the API server, generating a record hash at the API server, transmitting the identification hash, the record hash and the de-identified data from the API server to a core server, receiving the identification hash, the record hash and the de-identified data at the core server and transmitting the identification hash, the record hash and the de-identified data from the core server to a repository database to generate a record identification, transmitting the de-identified data, the record hash and the record identification from the repository database to the first client device, via the core server, generating a data hash by hashing the de-identified data and a plurality of attributes corresponding to the de-identified data and generating a register package based on the identification hash, the record hash and the data hash, storing the register package, from the core server, on to a blockchain to generate a transaction identification, transmitting the data hash and the transaction identification from the core server to the repository database, transmitting the transaction identification and the data hash to the first client device from the repository database, via the core server, regenerate the register package at the first client device based on the identification hash, the record hash and the data hash and verifying the register package with the blockchain by using the transaction identification, from the first client device.

According to a third aspect of the invention, there is provided a computer implemented method for facilitating secure management of data generated in an Electronic Health Record (EHR) during an episode of care, for a user, wherein the EHR is being maintained in a medical database comprised within a Healthcare Service Provider (HSP) server, the computer implemented method comprising the steps of receiving an identification hash corresponding to the user at an Application Program Interface (API) server from a first client device, extracting the data from the HSP server and de-identifying the data to obtain de-identified data, at the API server, generating a record hash at the API server; and transmitting the identification hash, the record hash and the de-identified data from the API server to a core server.

According to a fourth aspect of the invention, there is provided a computer implemented method for facilitating secure management of data generated in an Electronic Health Record (EHR) during an episode of care, for a user, wherein the EHR is being maintained in a medical database comprised within a Healthcare Service Provider (HSP) server, the computer implemented method comprising the steps of regenerate the register package at a first client device based on an identification hash, a record hash and a data hash, sending a record identification and a portion of the register package to a second client device, from the first client device, sending the record identification and the portion of the register package to the core server for retrieval of de-identified data, from the second client device, querying the repository database from the core server using the record identification and the portion of the register package and receiving a transaction identification, the identification hash, the record hash, the data hash and the de-identified data at the core server from the repository database in response to the query, sending, from the core server, at least one of the de-identified data and a first viewing medium to the second client device, the first viewing medium being configured for viewing of the de-identified data at the second client device, regenerating the register package at the core server based on the identification hash, the record hash and the data hash, sending the register package and the transaction identification from the core server to the second client device and verifying the register package with the blockchain using the transaction identification, from the second client device.

According to a fifth aspect of the invention, there is provided a computer implemented method for facilitating secure management of data generated in an Electronic Health Record (EHR) during an episode of care, for a user, wherein the EHR is being maintained in a medical database comprised within a Healthcare Service Provider (HSP) server, the computer implemented method comprising the steps of regenerating a register package at a first client device based on an identification hash, a record hash and a data hash, sending the register package and a transaction identification to a claims authorization server, verifying the register package with a blockchain from the claims authorization server, using the transaction identification and returning a confidence value from the claims authorization server to the first client device on verification of the register package.

According to a sixth aspect of the invention, there is provided a computer implemented method for facilitating secure management of data generated in an Electronic Health Record (EHR) during an episode of care, for a user, wherein the EHR is being maintained in a medical database comprised within a Healthcare Service Provider (HSP) server, the computer implemented method comprising the steps of generating a research query at a third client device, the research query comprising a plurality of characteristics, sending the research query to a core server from the third client device, verifying from the core server, of a presence of at least one characteristic from the plurality of characteristics, in de-identified data stored at a repository database, requesting the first client device for an access to the de-identified data from the core server, on verification of the presence of the at least one characteristic, receiving the record identification from the first client device in response to the request, at the core server and transmitting the record identification to a research database, from the core server, generating a research record hash at the core server, and transmitting the research record hash to the research database to be stored in association with the record identification, transmitting the research record hash to the third client device, querying the core server using the research record hash for viewing of the de-identified data, from the third client device, querying the research database from the core server using the research record hash and receiving the record identification at the core server from the research database, querying the repository database from the core server using the record identification and receiving the de-identified data at the core server from the repository database and sending, from the core server, a second viewing medium to the third client device, the second viewing medium being configured for viewing of the de-identified data at the third client device.

According to a seventh aspect of the invention, there is provided a system for secure management of data generated in an Electronic Health Record (EHR), during an episode of care, for a user, wherein the EHR is being maintained in a medical database comprised within a Healthcare Service Provider (HSP) server, the system comprising an Application Program Interface (API) server operably connected to the HSP server through a network, a core server operably connected to the API server through the network, a first client device having a first memory and a first processor, the first memory being operably connected to the first processor and the first client device being operably connected to the API server and the core server through the network, a repository database operably connected to the core server and a blockchain operably connected to the network. Further, the first memory is configured to store first computer program code, when executed by the first processor, enable the first processor to send an identification hash to the API server, receive de-identified data, a record hash and a record identification from the repository database, via the core server; and receive a transaction identification and a data hash from the repository database, via the core server. Further, the API server is configured to receive the identification hash from the first client device, generate a record hash, extract the data from the HSP server and de-identify the data to obtain de-identified data, transmit the identification hash, the record hash and the de-identified data to the core server. Further, the core server is configured to receive the de-identified data, the identification hash and the record hash from the API server and transmit the de-identified data, the identification hash and the record hash to the repository database to generate the record identification, transmit the de-identified data, the record hash and the record identification from the repository database to the first client device, generate the data hash by hashing the de-identified data and a plurality of attributes corresponding to the de-identified data and generate a register package based on the data hash, the identification hash and the record hash, store the register package on to the blockchain to generate the transaction identification, transmit the data hash and the transaction identification to the repository database and transmit the transaction identification and the data hash from the repository database to the first client device.

In one embodiment of the invention, the first computer program code further enables the first processor to generate an asymmetrical pair of a public key and a private key, concatenate a first nonce to the public key to obtain a first resultant string, and apply a hashing algorithm to the first resultant string to obtain a user hash, receive a second nonce from the core server and concatenate the second nonce to the user hash to generate a second resultant string and apply the hashing algorithm to the second resultant string to generate the identification hash. Further, the core server is further configured to generate the second nonce corresponding to the user hash and transmit the second nonce to the first client device.

In one embodiment of the invention, the identification hash is sent to the API server through a first offline communication medium.

In one embodiment of the invention, the first offline communication medium is selected from a group including Quick Response (QR) code, Near Field Communication (NFC) and Bluetooth.

In one embodiment of the invention, the first computer program code further enables the first processor to display one or more first details corresponding to the user to allow verification of an identity of the user.

In one embodiment of the invention, the plurality of attributes comprise a geographical location tag and a time stamp.

In one embodiment of the invention, the first processor is enabled to receive the de-identified data, the record identification, the transaction identification, the record hash and the data hash from the core server in response to sending the identification hash to the core server.

In one embodiment of the invention, the first computer program code, further enables the first processor to regenerate the register package based on the identification hash, the record hash and the data hash and verify the register package with the blockchain by using the transaction identification.

In one embodiment of the invention, the core server is further configured to verify the de-identified data with the first client device after transmitting the de-identified data to the first client device.

In one embodiment of the invention, the core server is further configured to verify the register package with the first client device, before storing the register package on to the blockchain.

In one embodiment of the invention, the system further comprising a second client device operably connected to the network, and having a second memory and a second processor, the second memory being operably connected to the second processor. Further, the second memory is configured to store a second computer program code, the second program code when executed by the second processor, enable the second processor to receive the record identification and a portion of the register package from the first client device, send the record identification and the portion of the register package to the core server for retrieval of the de-identified data and receive, from the core server, at least one of the de-identified data and a first viewing medium at the second client device, the first viewing medium being configured for viewing of the de-identified data at the second client device. Further, the first computer program code further enables the first processor to regenerate the register package based on the identification hash, the record hash and the data hash and send the record identification and the portion of the register package to the second client device. Further, the core server is further configured to receive the record identification and the portion of the register package from the second client device, query the repository database using the record identification and the portion of the register package and receive the transaction identification, the identification hash, the record hash, the data hash and the de-identified data from the repository database in response to the query and send at least one of the de-identified data and the first viewing medium to the second client device.

In one embodiment of the invention, the second processor is further enabled to receive the register package and the transaction identification from the core server and verify the register package with the blockchain using the transaction identification. Further, the core server is further configured to regenerate the register package based on the identification hash, the record hash and the data hash and transmit the register package and the transaction identification to the second client device.

In one embodiment of the invention, the core server is further configured to regenerate the register package based on the identification hash, the record hash and the data hash and verify the regenerated register package with the portion of the register package received from the second client device.

In one embodiment of the invention, the record identification and the portion of register package are sent to the second client device through a second offline communication medium.

In one embodiment of the invention, the second offline communication medium is selected from a group including Quick Response (QR) code, Near Field Communication (NFC) and Bluetooth.

In one embodiment of the invention, the first computer code further enables the first processor to send one or more second details corresponding to the user for verification of an identity of the user.

In one embodiment of the invention, the system further comprising a claims authorization server. Further, the first processor is further enabled to to regenerate the register package based on the identification hash, the record hash and the data hash to regenerate the register package, send the register package and the transaction identification to the claims authorization server and receive a confidence value from the claims authorization server. Further, the claims authorization server is configured to verify the register package with the blockchain, using the transaction identification and return the confidence value to the first client device on verification of the register package.

In one embodiment of the invention, the system further comprising a research database operably connected to the network and a third client device operably connected to the network, and having a third memory and a third processor, the third memory being operably connected to the third processor. Further, the third memory is configured to store a third computer program code, the third program code when executed by the third processor, enables the third processor to generate a research query, the research query comprising a plurality of characteristics, send the research query to the core server and receive a research record hash from the core server. Further, the core server is further configured to verify a presence of at least one characteristic from the plurality of characteristics, in the de-identified data stored at the repository database, request the first client device for an access to the de-identified data, on verification of the presence of the at least one characteristic, receive the record identification from the first client device in response to the request and transmit the record identification to the research database, generate the research record hash and transmit the research record hash to the research database to be stored in association with the record identification, and transmit the research record hash to the third client device. Further, the first computer program code further enables the first processor to receive the request for the access to the de-identified data and transmit the record identification to the core server in response to the request.

In one embodiment of the invention, the third computer program code further enables the third processor to query the core server using the research record hash for viewing of the de-identified data and receive a second viewing medium at the third client device, in response to the query, the second viewing medium being configured for viewing of the de-identified data at the third client device. Further, the core server is further configured to receive the research record hash from the third client device, query the research database using the research record hash and receive the record identification from the research database, query the repository database using the record identification and receive the de-identified data at the core server from the repository database and send the second viewing medium to the third client device.

In one embodiment of the invention, the first processor is enabled to receive the request for access to the de-identified data on sending the identification hash to the core server.

According to an eighth aspect of the invention, there is provided a system for secure management of data generated in an Electronic Health Record (EHR) during an episode of care, for a user, wherein the EHR is being maintained in a medical database comprised within a Healthcare Service Provider (HSP) server, the system comprising an Application Program Interface (API) server operably connected to the HSP server, a core server operably connected to the API server through a network, a first client device having a first memory and a first processor and operably connected to the API server and the core server through the network, a repository database operably connected to the core server and a blockchain operably connected to the network. Further, the first memory is configured to store a first computer program code, when executed by the first processor, enable the first processor to send an identification hash to the API server, receive de-identified data, a record hash and a record identification from the repository database, via the core server, receive a transaction identification and a data hash from the repository database, via the core server, regenerate a register package based on the identification hash, the record hash and the data hash and verify the register package with the blockchain by using the transaction identification. Further, the API server is configured to receive the identification hash from the first client device, extract the data from the HSP server and de-identify the data to obtain the de-identified data, generate the record hash and transmit the identification hash, the record hash and the de-identified data to the core server. Further, the core server is configured to receive the identification hash, the record hash and the de-identified data from the API server and transmit the identification hash, the record hash and the de-identified data to the repository database to generate the record identification, transmit the de-identified data, the record hash and the record identification from the repository database to the first client device, generate a data hash by hashing the de-identified data and a plurality of attributes corresponding to the de-identified data, and generate the register package based on the identification hash, the record hash and the data hash, store the register package on to the blockchain to generate the transaction identification, transmit the data hash and the transaction identification to the repository database and transmit the transaction identification and the data hash from the repository database to the first client device.

According to a ninth aspect of the invention, there is provided a core server for facilitating secure management of data generated in an Electronic Health Record (EHR), during an episode of care, for a user, wherein the EHR is being maintained in a medical database comprised within a Healthcare Service Provider (HSP) server, the core server configured to receive de-identified data, an identification hash and a record hash from the API server and transmit the identification hash, the record hash and the de-identified data to a repository database to generate a record identification, transmit the de-identified, the record hash and the record identification from the repository database to a first client device, generate a data hash by hashing the de-identified data and a plurality of attributes corresponding to the de-identified data and generate a register package based on the data hash, the identification hash and the record hash, store the register package onto a blockchain to generate a transaction identification, transmit the data hash and the transaction identification to a repository database and transmit the transaction identification and the data hash from the repository database to the first client device.

In one embodiment of the invention, the core server is further configured generate a second nonce corresponding to a user hash and transmit the second nonce to the first client device.

In one embodiment of the invention, the plurality of attributes comprise a geographical location tag and a time stamp.

In one embodiment of the invention, the core server is further configured to verify the de-identified data with the first client device after transmitting the de-identified data to the first client device.

In one embodiment of the invention, the core server is further configured to verify the register package with the first client device, before storing the register package on to the blockchain.

In one embodiment of the invention, the core server is further configured to receive the record identification and a portion of the register package for retrieval of the de-identified data, from a second client device, query the repository database using the record identification and the portion of the register package and receive the transaction identification, the identification hash, the record hash, the data hash and the de-identified data from the repository database in response to the query and send at least one of the de-identified data and a first viewing medium to the second client device, the first viewing medium being configured for viewing of the de-identified data at the second client device.

In one embodiment of the invention, the core server is further configured to regenerate the register package based on the identification hash, the record hash and the data hash and send the register package and the transaction identification to the second client device.

In one embodiment of the invention, the core server is further configured to regenerate the register package based on the identification hash, the record hash and the data hash and verify the regenerated register package with the portion of the register package received from the second client device.

In one embodiment of the invention, the core server is further configured to receive a research query from a third client device, the research query comprising a plurality of characteristics, verify a presence of at least one characteristic from the plurality of characteristics, in the de-identified data stored at the repository database, request the first client device for an access to the de-identified data, on verification of the presence of the at least one characteristic, receive the record identification from the first client device in response to the request and transmit the record identification to a research database, generate a research record hash and transmit the research record hash to the research database to be stored in association with the record identification and transmit the research record hash to the third client device.

In one embodiment of the invention, the core server is further configured to receive receive the research record hash from the third client device for viewing of the de-identified data, query the research database using the research record hash and receive the record identification from the research database, query the repository database using the record identification and receive the de-identified data at the core server from the repository database and send a second viewing medium to the third client device, the second viewing medium being configured for viewing of the de-identified data at the third client device.

According to a tenth aspect of the invention, there is provided an API server for facilitating secure management of data generated in an Electronic Health Record (EHR), during an episode of care, for a user, wherein the EHR is being maintained in a medical database comprised within a Healthcare Service Provider (HSP) server, the API server being configured to receive an identification hash corresponding to the user from a first client device, extract the data from the HSP server and de-identify the data to obtain de-identified data, generate a record hash and transmit the identification hash, the record hash and the de-identified data to a core server.

According to an eleventh aspect of the invention, there is provided a second client device for facilitating secure management of data generated in an Electronic Health Record (EHR), during an episode of care, for a user, wherein the EHR is being maintained in a medical database comprised within a Healthcare Service Provider (HSP) server, the second client device comprising a second memory operably connected to a second processor, the second memory comprising a second computer program code stored thereon, the second program code when executed by the second processor, enables the second processor to receive a record identification and a portion of a register package from a first client device, send the record identification and the portion of the register package to a core server for retrieval of de-identified data, receive, from the core server, at least one of the de-identified data and a first viewing medium at the second client device, the first viewing medium being configured for viewing of the de-identified data at the second client device, receive the register package and a transaction identification from the core server and verify the register package with the blockchain using the transaction identification.

According to a twelfth aspect of the invention, there is provided a system for facilitating secure management of data generated in an Electronic Health Record (EHR) during an episode of care, for a user, wherein the EHR is being maintained in a medical database comprised within a Healthcare Service Provider (HSP) server, the system comprising a first client device having a first processor and a first memory, the first processor being operably connected to the first memory, a claims authorization server operably connected to the first client device through a network. Further the first memory comprises a first computer program code, the first computer program code when executed by the first processor, enables the first processor to regenerate a register package based on an identification hash, a record hash and a data hash, send the register package and a transaction identification to the claims authorization server and receive a confidence value from the claims authorization server. Further, the claims authorization server is configured to verify the register package with a blockchain, using the transaction identification and return the confidence value to the first client device on verification of the register package.

According to a thirteenth aspect of the invention, there is provided a system for facilitating secure management of data generated in an Electronic Health Record (EHR) during an episode of care, for a user, wherein the EHR is being maintained in a medical database comprised within a Healthcare Service Provider (HSP) server, the system comprising a first client device having a first processor and a first memory, the first processor being operably connected to the first memory, a third client device having a third processor and a third memory, the third processor being operably connected to the third memory, a core server operably connected to the third client device through a network, a repository database operably connected to the core server and a research database operably connected to the network. Further, the third memory comprises a third computer program code, the third computer program code when executed by the third processor, enables the third processor to generate a research query, the research query comprising a plurality of characteristics, send the research query to the core server and receive a research record hash from the core server, query the core server using the research record hash for viewing of the de-identified data and receive a second viewing medium at the third client device, in response to the query, the second viewing medium being configured for viewing of the de-identified data at the third client device. Further, the core server is configured to verify a presence of at least one characteristic from the plurality of characteristics, in the de-identified data stored at the repository database, request the first client device for an access to the de-identified data, on verification of the presence of the at least one characteristic, receive a record identification from the first client device in response to the request and transmit the record identification to the research database, generate the research record hash and transmit the research record hash to the research database to be stored in association with the record identification, transmit the research record hash to the third client device, receive the research record hash from the third client device, query the research database using the research record hash and receive the record identification from the research database, query the repository database using the record identification and receive the de-identified data at the core server from the repository database and send the second viewing medium to the third client device. Further, the first memory comprises a first computer program code, the first computer program code when executed by the first processor, enables the first processor to receive the request for the access to the de-identified data and transmit the record identification to the core server in response to the request.

In one embodiment of the invention, the first processor is enabled to receive the request for access to the de-identified data on sending an identification hash to the core server.

According to a fourteenth aspect of the invention, there is provided a claims authorization server for facilitating secure management of data generated in an Electronic Health Record (EHR) during an episode of care, for a user, wherein the EHR is being maintained in a medical database comprised within a Healthcare Service Provider (HSP) server, wherein the claims authorization server is configured to receive a register package and a transaction identification from a first client device, verify the register package with a blockchain, using the transaction identification and return a confidence value to the first client device on verification of the register package.

Other aspects of the invention are also disclosed.

BRIEF DESCRIPTION OF THE DRAWINGS

Notwithstanding any other forms which may fall within the scope of the present invention, a preferred embodiment/preferred embodiments of the invention will now be described, by way of example only, with reference to the accompanying drawings in which.

DESCRIPTION OF EMBODIMENTS

Figure 1:
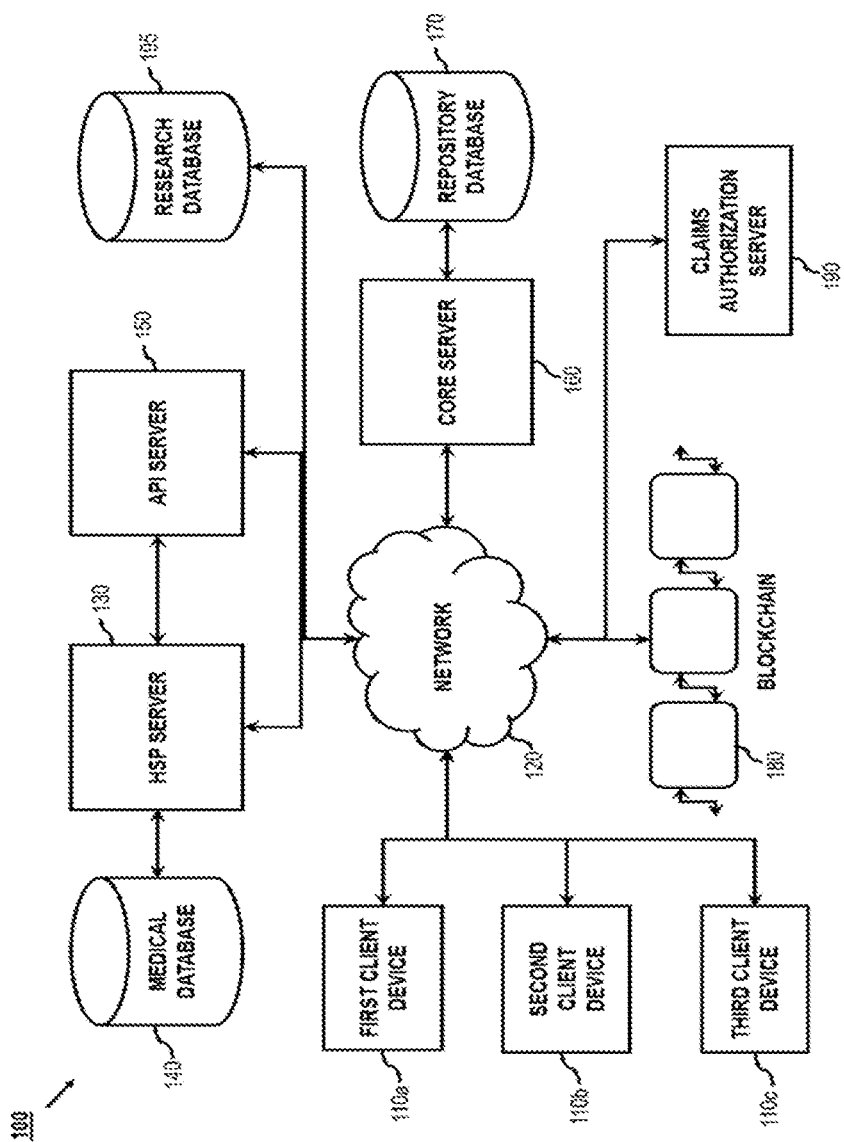
FIG. 1 illustrates a top level diagram of a system of computing devices to which various embodiments described herein may be implemented.

It should be noted in the following description that like or the same reference numerals in different embodiments denote the same or similar features.
System 100 of Computing Devices FIG. 1 shows a system 100 of computing devices adapted for implementation of various embodiments of the present invention.

As such, the system 100 comprises a Healthcare Service Provider (HSP) server 130 operably connected to a network 120. Preferably, the network 120 is internet. The HSP server 130 maintains a medical database 140. The medical database 140 stores an Electronic Health Record (EHR) for a user. During an episode of care, for the user, data is generated and stored in the EHR. The medical database 140 is configured to store the data in a plurality of formats, including, but not limited to, FHIR and HL7.

An Application Program Interface (API) server 150 is operably connected to the HSP server 130 through the network 120. Further, the API server 150 is operably connected also to a core server 160 through the network 120. The core server 160 is further operably connected to a repository database 170. In one embodiment of the invention, the repository database 170 is configured to process queries in Structured Query Language (SQL) format. Further, a blockchain 180 is operably connected to the network 120. Further, a claims authorization server 190 is operably connected to the network 120. Also, a research database 195 is operably connected to the network 120. In one embodiment of the invention, the research database 195 is configured to process queries in SQL format.

A plurality of client devices 110 (for e.g. 110a, 110b and 110c) are also operably connected to the network 120. In one embodiment of the invention, the plurality of client devices 110 are from a group of, but not limited to, a mobile handheld device, a personal computer, a laptop and a tablet etc.

Figure 2:
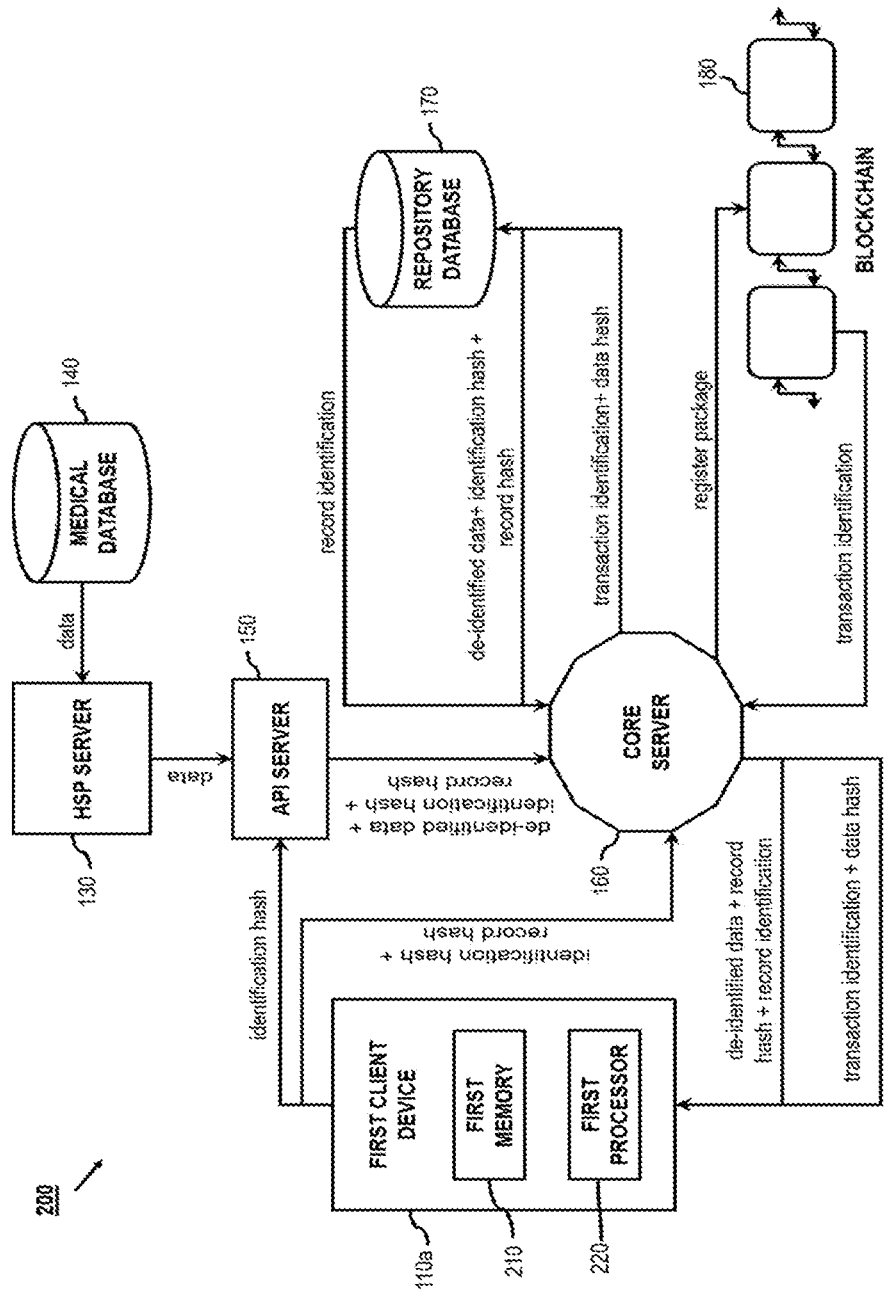
FIG. 2 illustrates an information flow diagram for de-identification of data and receiving of de-identified data at a first client device, in accordance with a preferred embodiment of the present invention.

A system for secure management of data generated in the EHR during an episode of care makes use of the computing devices as described above. FIG. 2 illustrates a flow of information between the computing devices of system 100. In one embodiment of the invention, a first client device 110a from the plurality of client devices 110, comprises a first memory 210 and a first processor 220. The first memory 210 being operably connected to the first processor 220. Further, the first memory 210 is configured to store a first computer program code. The first memory 210 is also configured to store an identification hash. The identification hash is a unique hash value corresponding to the first client device 110a. In one embodiment of the invention, the identification hash is provided to the first client device 110a through the first computer program code. Alternately, the identification hash is generated by the first client device 110a.

Figure 3:
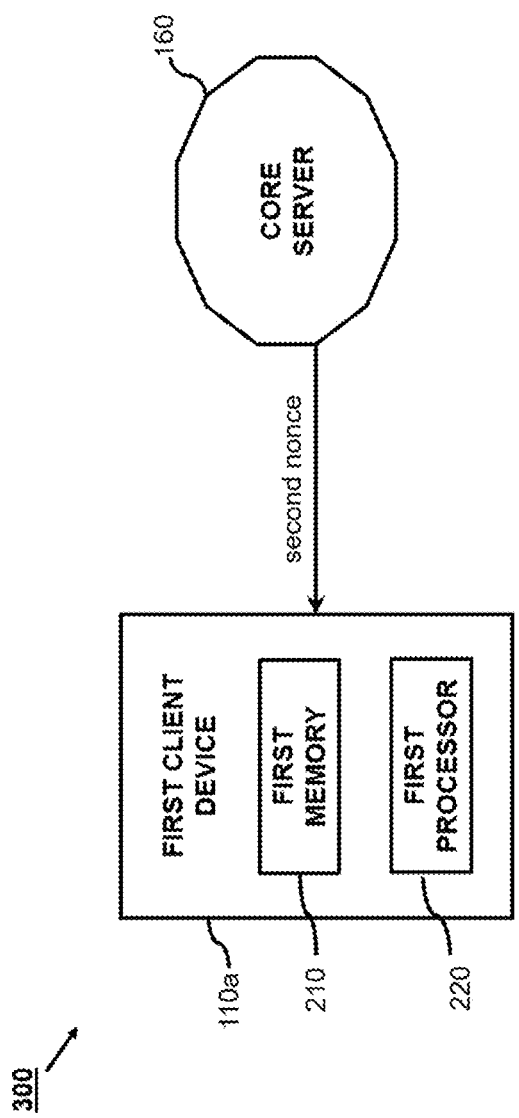
FIG. 3 illustrates an information flow diagram for generation of an identification hash at the first client device, in accordance with a preferred embodiment of the present invention.

FIG. 3 illustrates an information flow for generation of the identification hash at the first client device 110a. In accordance with the embodiment, the first computer program code, when executed by the first processor 220, enables the first processor 220 to generate an asymmetrical pair of a public key and a private key. In one embodiment of the invention, the asymmetrical pair of the public key and the private key is generated from Elliptical Curve Digital Signature (ECDS) algorithm. Further, the private key is stored in a secure area at the first client device 110a. Storing the private key inside a secure area provides a layer of hardware protection for the private key. Further, the first processor 220 is further enabled to concatenate a first nonce to the public key to generate a first resultant string, the first nonce having a high entropy characteristic. Further, the first computer program code enables the first processor 220 to apply a hashing algorithm to the first resultant string to obtain a user hash. In one embodiment of the invention the hashing algorithm is, but not limited to, SHA256. The user hash is sent by the first processor 220 to the core server 160.

In accordance with the embodiment, the core server 160 is configured to generate a second nonce corresponding to the user hash, the second nonce also having the high entropy characteristic. Further, the core server 160 is configured to transmit the second nonce to the first client device 110a. The first computer program code enables the first processor 220 to receive the second nonce at the first client device 110a. Further, the first processor 220 is enabled to concatenate the second nonce to the user hash to generate a second resultant string. Further, the first processor 220 is enabled to apply the hashing algorithm to the second resultant string to obtain the identification hash.

The second nonce is then stored by the first processor 220 in the first memory 210 in association with the public key. It is to be noted that no record of the second nonce are maintained at the core server 160. The deletion of the second nonce ensures that, in case the core server 160 is hacked, the second nonce will not be stolen from the core server 160. Further, deletion of the second nonce also constitutes to good housekeeping, and thus storage space at the core server 160 is not wasted.

With respect to FIG. 2, the first computer program code further enables the first processor 220 to send the identification hash to the API server 150. In one embodiment of the invention, the identification hash is sent to the API server 150 through a first offline communication medium. Further, the first offline communication medium is selected from a group of technologies that are able to carry the identification hash, including but not limited to, Quick Response (QR) code, Near Field Communication (NFC) and Bluetooth. The use of the first offline communication medium ensures that the identity of the first client device 110a is not disclosed to the API server 150.

In one embodiment of the invention, the first computer program code further enables the first processor 220 to display one or more first details corresponding to the user to allow verification of an identity of the user. The one or more first details include, but are not limited to, name, age, sex and bio-metric data of the user. In one embodiment of the invention, the identity of the user is verified by a receptionist available with the API server 150. In accordance with another embodiment, the API server 150 comprises an in-built module for verification of the identity of the user.

The API server 150 is configured to receive the identification hash from the first client device 110*a*. In one embodiment of the invention, on receiving the identification hash, the API server 150 stores the identification hash in association with the identity of the user, at an API server memory provided at the API server 150. Further, the API server 150 is configured to extract the data generated in the EHR, during the episode of care, from the HSP server 130. In one embodiment of the invention, the API server 150 prompts the HSP server 130 for the data, with the one or more first details of the user. The HSP server 130 then queries the medical database 140 for the data. On receiving the data from the medical database 140, the HSP server 130 transmits the data to the API server 150.

The API server 150 is then configured to de-identify the data to obtain de-identified data. In one embodiment of the invention, de-identifying data includes removal of all the fields from the data, which may lead to identification of the user through a system, a device or any other person. The API server 150 is further configured to generate a record hash from the core server 160. The record hash corresponds to a record being generated during an instance of the functioning of the system. The API server 150 is then configured to transmit the de-identified data, the record hash and the identification hash to the core server 160.

The core server 160 is configured to receive the de-identified data, the record hash and the identification hash from the API server 150. Further, the core server 160 is configured to transmit the de-identified data, the record hash and the identification hash to the repository database 170 to generate a record identification. The record identification is sent from the repository database 170 to the core server 160. Further, the core server 160 is configured to transmit the de-identified data, the record hash and the record identification to the first client device 110*a* from the repository database 170. It is to be noted that, the de-identified data, the record hash and the record identification are not "pushed" to the first client device 110*a*. In other words, the de-identified data, the record hash and the record identification are not immediately transmitted to the first client device 110*a*. It is an important security feature, as it will discourage any hacker to steal the de-identified data through attacks such as MITM attacks. In one embodiment of the invention, a first flag is set at the core server 160 corresponding to the identification hash.

The first computer program code enables the first processor 220 to synchronize with the core server 160. In one embodiment of the invention, the first processor 220 synchronizes with the core server 160 during an event of initiation of execution of the first computer program code. In accordance with another embodiment, the first processor 220 synchronizes with the core server 160 periodically. When the first processor 220 becomes aware of the first flag, the first processor 220 can receive (or "pull") the de-identified data, the record hash and the record identification from the repository database 170. In one embodiment of the invention, the first processor 220 is enabled by the first computer program code, to receive the de-identified data, the record hash and the record identification in response to sending the identification hash to the core server 160. The core server 160 is then configured to query the repository database 170 using the identification hash and receive the de-identified data, the record hash and the record identification at the core server 160. The core server 160 is configured to then transmit the de-identified data, the record hash and the record identification to the first client device 110*a*. The first computer program code enables the first processor 220 to receive the de-identified data, the record hash and the record identification from the core server 160.

In one embodiment of the invention, the core server 160 is further configured to verify the de-identified data with the first client device 110*a* after transmitting the de-identified data to the first client device 110*a*. In one embodiment of the invention, the de-identified data is displayed to the user for verification. In accordance with another embodiment, the de-identified data is verified automatically by the first processor 220 through execution of the first computer program code.

In one embodiment of the invention, the first processor 220 is further enabled to transmit the identification hash and the record hash to the core server 160. The core server 160 is configured to then query the repository database 170 using the record hash and the identification hash and receive the de-identified data from the repository database 170, in response to the query. The core server 160 is further configured to generate a data hash by hashing the de-identified data and a plurality of attributes corresponding to the de-identified data. In one embodiment of the invention, the plurality of attributes comprise a geographical location tag and a time stamp. In accordance with another embodiment, the plurality of attributes comprise SNOMED codes and LOINC codes corresponding to the de-identified data. The core server 160 is further configured to generate a register package based on for example by fusing the identification hash, the record hash and the data hash. Further, the core server 160 is configured to store the register package, for example by mining the register package, onto the blockchain 180 to generate a transaction identification.

In one embodiment of the invention, the core server 160 is further configured to verify the register package with the first client device 110*a* before storing (for example, mining) the register package onto the blockchain 180. In accordance with the embodiment, the first computer program code enables the first processor 220 to regenerate the identification hash from the private key using the ECDS algorithm, the first nonce, the second nonce and the hashing algorithm. Further, the first processor 220 is enabled to transmit the identification hash to the core server 160. The core server 160 is configured to use the identification hash received from the first client device 110*a* to generate a second instance of the register package. If the second instance of the register package matches the register package generated at the core server 160, the register package is verified.

In one embodiment of the invention, the blockchain 180 is a database having a plurality of data structures known as blocks. When the register package is stored onto the blockchain 180, a new block is created. The creation of the new block also constitutes to generation of the transaction identification. The new block comprises the register package, the transaction identification and a hash of a previous block. In this way, the new block is linked to the previous block. The linking of the plurality of blocks gives the blockchain 180, a chain like structure.

The blockchain 180 acts as a de-centralized log and the register package acts as an individual entry in the de-centralized log. Since the register package is obtained based on the identification hash, the record hash and the data hash, the register package is unique to the user, the record generated for that instance of functioning of the system and the de-identified data. This way a plurality of users can create a plurality of individual entries pertaining to a plurality of records. The blockchain 180 is configured to return the register package, when queried by any of the computing devices of system 100, using the transaction identification.

The core server 160 is then configured to transmit the data hash and the transaction identification to the repository database 170. In one embodiment of the invention, a second flag is set at the core server 160 corresponding to the identification hash.

The first computer program code enables the first processor 220 to synchronize with the core server 160. In one embodiment of the invention, the first processor 220 synchronizes with the core server 160 during an event of initiation of execution of the first computer program code. In accordance with another embodiment, the first processor 220 synchronizes with the core server 160 periodically. When the first processor 220 becomes aware of the second flag, the first processor 220 can receive (or "pull") the transaction identification and the data hash from the repository database 170.

In one embodiment of the invention, the first processor 220 is enabled by the first computer program code, to receive the transaction identification and the data hash in response to sending the identification hash to the core server 160. The core server 160 is configured to then query the repository database 170 using the identification hash and receive the transaction identification and the data hash from the repository database 170. The core server 160 is configured to then transmit the transaction identification and the data hash to the first client device 110a. The first computer program code enables the first processor 220 to receive the transaction identification and the data hash from the core server 160.

It is to be noted that no record of the transaction identification and the data hash is kept at the core server 160 for security of the transaction identification and the data hash.

Further, the first computer program code further enables the first processor 220 to receive the record identification, the transaction identification, the record hash and the data hash from the core server 160 and store the record identification, the transaction identification, the record hash and the data hash in the first memory 210. In one embodiment of the invention, the first computer program code further enables the first processor 220 to regenerate the register package base on for example by fusing the identification hash, the record hash and the data hash. Further, the first computer program code enables the first processor 220 to verify the register package with the blockchain 180, using the transaction identification. In one embodiment of the invention, the first processor 220 verifies the register package using a plurality of blockchain utilities. In one embodiment of the invention, the first processor 220 verifies the register package using other blockchain address parameters.

Figure 4:
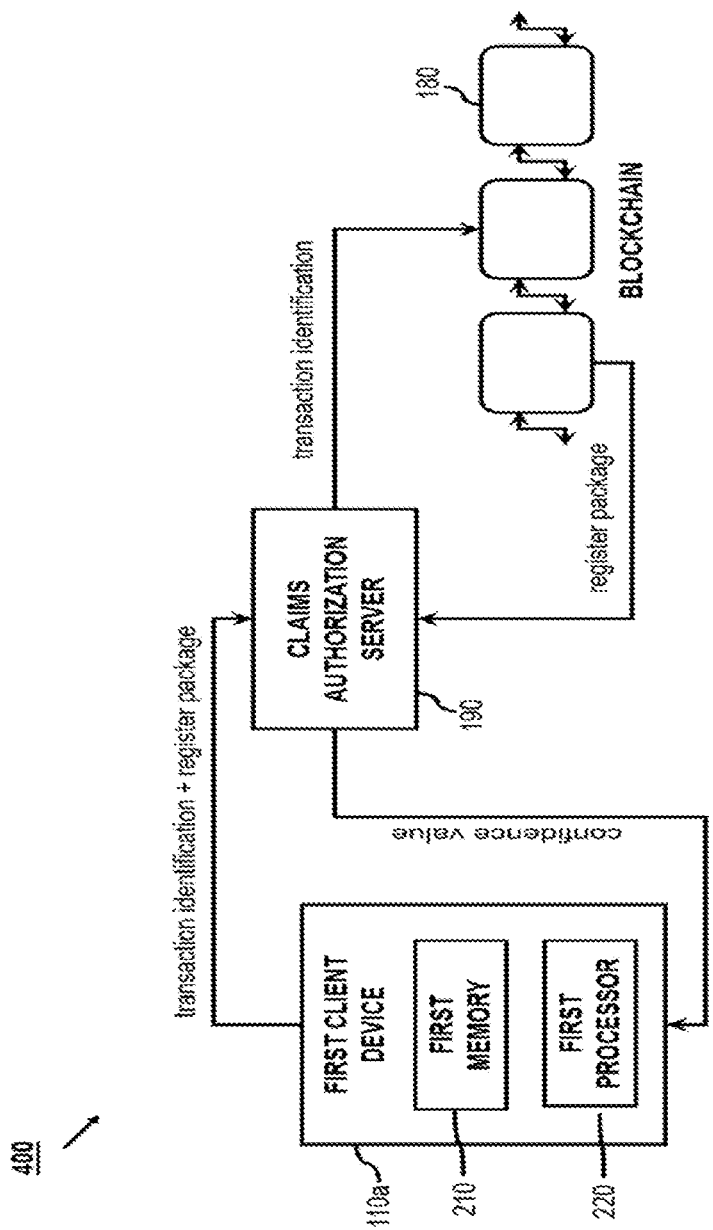
FIG. 4 illustrates an information flow diagram for authorization of an insurance claim using a claims authorization server, in accordance with a preferred embodiment of the present invention.

In one embodiment of the invention, the user may wish to claim an insurance amount from an insurance company for the episode of care. The insurance company may necessitate that the user verifies the episode of care with the claims authorization server 190. Further, the insurance may demand provision of a confidence value from the user using the first client device 110a. FIG. 4 illustrates an information flow diagram in accordance with the embodiment. As shown in FIG. 4, the first processor 220 is further enabled by the first computer program code to regenerate the register package based on for example by fusing the identification hash, the record hash and the data hash. Further, the first processor 220 is enabled to send the register package and the transaction identification to the claims authorization server 190 and receive the confidence value from the claims authorization server 190.

In turn, the claims authorization server 190 is configured to verify the register package with the blockchain 180, using the transaction identification. Further, the claims authorization server 190 is configured to send the confidence value to the first client device 110a on verification of the register package.

Figure 5:
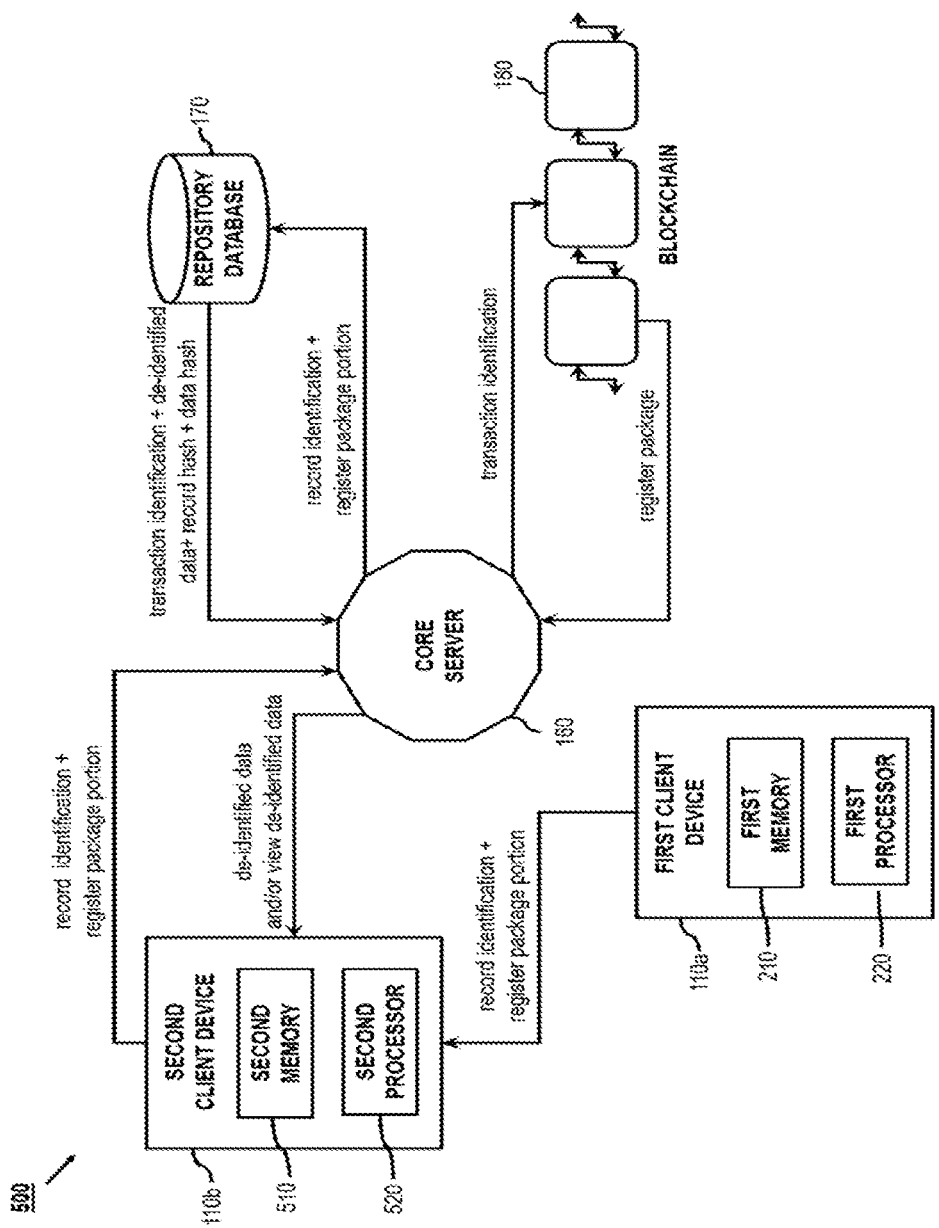
FIG. 5 illustrates an information flow diagram for viewing of the de-identified data at a second client device, in accordance with a preferred embodiment of the present invention.

The user may want to securely share the de-identified data with a second user. The second user may be a doctor or a pharmacist who is interested in viewing the de-identified data to write a prescription to the user or to sell a drug prescribed by the doctor, respectively. Further, the second user may opt to view the de-identified data at a second client device 110b from the plurality of client devices 110. FIG. 5 illustrates an information workflow for receiving of the de-identified data at the second client device 110b. In that case, the first computer program code enables the first processor 220 to regenerate the register package based on for example by fusing the identification hash, the record hash and the data hash. Further, the first computer program code enables the first processor 220 to send a portion of the register package and the record identification to the second client device 110b.

In one embodiment of the invention, the portion of the register package and the record identification are sent to the second client device 110b through a second offline communication medium. Further, in one embodiment of the invention, the second offline communication medium is selected from a group of technologies that are able to carry the portion of the register package and the record identification, including but not limited to, Quick Response (QR) code, Near Field Communication (NFC) and Bluetooth. The use of the second offline communication medium ensures that the identity of the first client device 110a is not intercepted. Further, the first computer code further enables the first processor 220 to provide one or more second details corresponding to the user for verification of an identity of the user. In one embodiment of the invention, the one or more second details comprise, but are not limited to, name, age, sex, biometric data and address of the user. In one embodiment of the invention, the one or more second details are displayed to the second user at the first client device 110a. In accordance with another embodiment, the one or more second details are transmitted to the second client device 110b through the second offline communication medium.

In one embodiment of the invention, the second client device 110b is having a second memory 510 and a second processor 520, the second memory 510 being operably connected to the second processor 520. Further the second computer program code when executed by the second processor 520, enables the second processor 520 to receive the register package from the first client device 110a. Further, the second computer program code enables the second processor 520 to send the record identification and the portion of the register package to the core server 160 for retrieval of the de-identified data.

The core server 160 is then configured to receive the record identification and the portion of the register package from the second client device 110b. The core server 160 is further configured to query the repository database 170 using the record identification and the portion of the register package and receive the transaction identification, the identification hash, the record hash, the data hash and the de-identified data from the repository database 170 in response to the query.

In one embodiment of the invention, the core server 160 is further configured to regenerate the register package based on for example by fusing the identification hash, the record hash and the data hash. Further, the core server 160 is configured to verify the regenerated register package with the portion of the register package received from the second client device 110*b*. Further, the core server 160 is configured to send at least one of the de-identified data and a first viewing medium to the second client device 110*b*, the first viewing medium being configured for viewing of the de-identified data at the second client device 110*b*.

The de-identified data is transmitted when a size of the de-identified data is small enough to be transmitted. In an embodiment, where de-identified data has too large a size for transmission, only the first viewing medium is provided to the second client device 110*b*. In another embodiment, de-identified data is transmitted partly and the remaining part is sent through the first viewing medium. In one embodiment of the invention, the core sever 160 is configured to provide the first viewing medium only on successful verification of the register package with the portion of the register package.

The second computer program code then enables the second processor 520 to receive, from the core server 160, at least one of the de-identified data and the first viewing medium at the second client device 110*b*. In one embodiment of the invention, the core server 160 is further configured to transmit the register package and the transaction identification to the second client device 110*b*. Further, the second processor 520 is further enabled to receive the register package and the transaction identification from the core server 160. Also the second processor 520 is further enabled to, verify the register package with the blockchain 180 using the transaction identification.

Figure 6A:
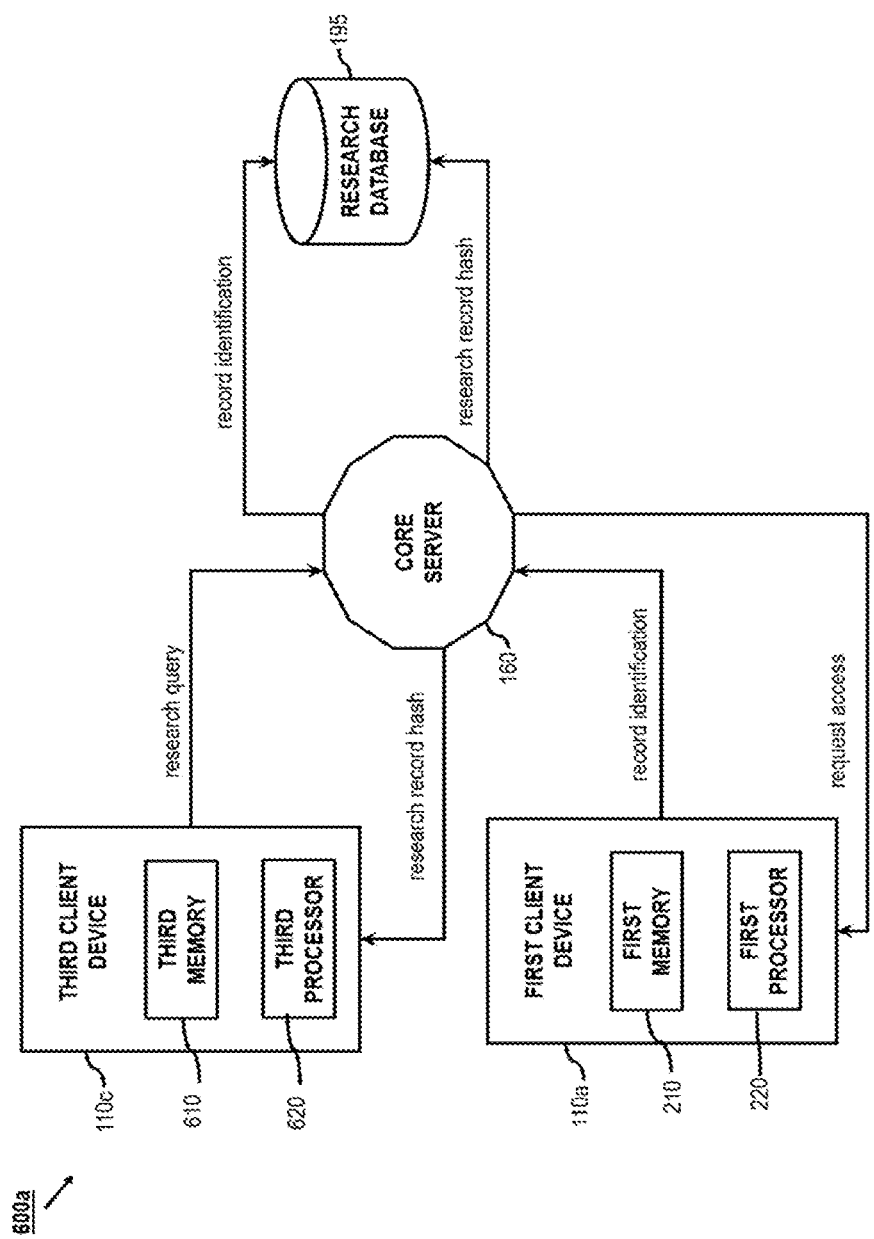
FIG. 6a illustrates an information flow diagram for generation of a research record, in accordance with a preferred embodiment of the present invention.
Figure 6B:
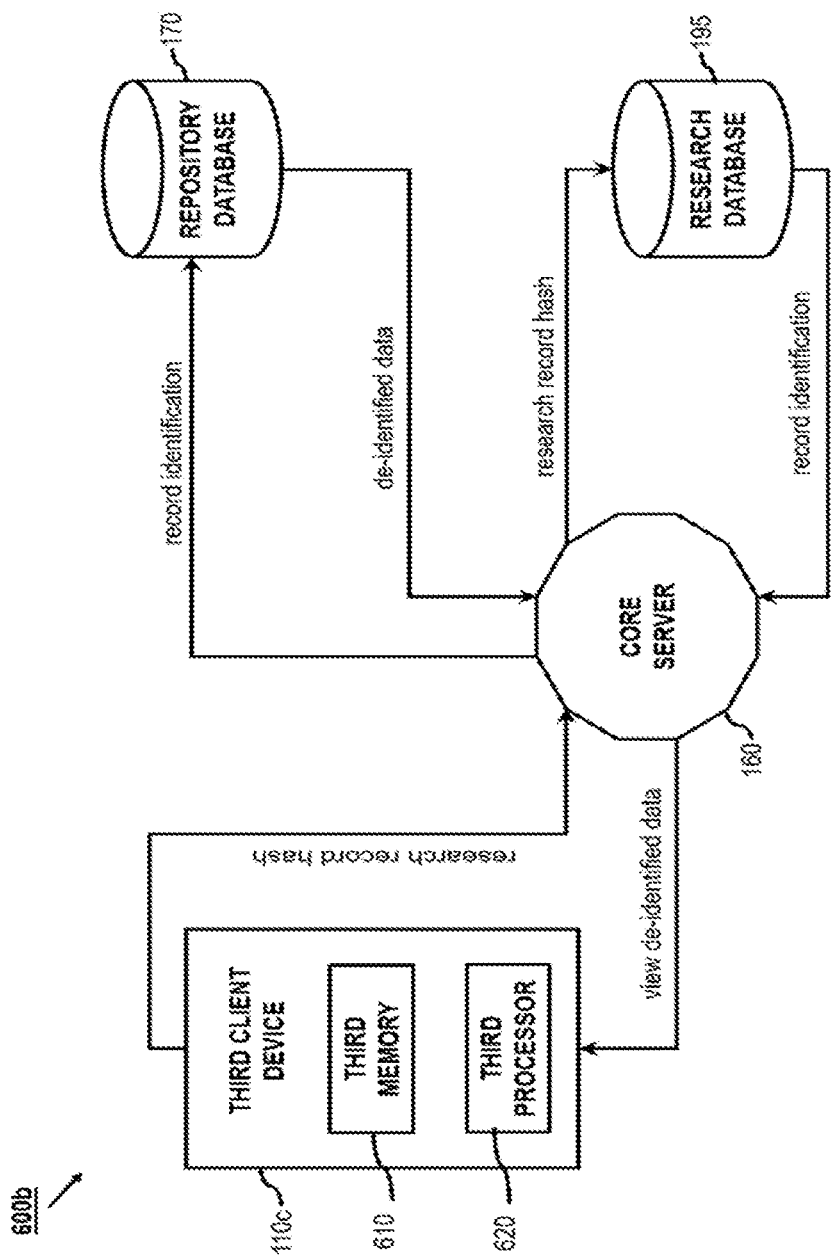
FIG. 6b illustrates an information flow diagram for viewing of the de-identified data by a researcher using a third client device, in accordance with a preferred embodiment of the present invention.

In one embodiment of the invention, a researcher may want to view the de-identified data for conducting disease research, epidemiological studies and surveys etc. Further, the researcher may want to view the de-identified data at a third client device 110*c* from the plurality of client devices 110, operably connected to the network 120. FIGS. 6*a* and 6*b* illustrate information flow diagrams for generation of a research record and viewing of the de-identified data, respectively, in accordance with the embodiment. As shown in FIGS. 6*a* and 6*b*, the third client device 110*c* is having a third memory 610 and a third processor 620, the third memory 610 being operably connected to the third processor 620. Further, the third memory 610 is configured to store a third computer program code, the third program code when executed by the third processor 620, enables the third processor 620 to generate a research query, the research query comprising a plurality of characteristics. In one embodiment of the invention, the plurality of characteristics comprise filter data such as, but not limited to, a general interest, a medical disease, gender, geographical region and time period etc.

Further, the third processor 620 is enabled to send the research query to the core server 160. The core server 160 is then configured to verify a presence of at least one characteristic from the plurality of characteristics, in the de-identified data stored at the repository database 170. Further, the core server 160 is configured to request the first client device 110*a* for an access to the de-identified data, on verification of the presence of the at least one characteristic. In accordance with an embodiment, a third flag is set in at the core server 160, corresponding to the identification hash.

In one embodiment of the invention, the first computer program code enables the first processor 220 to receive the request for the access to the de-identified data. When the first processor 220 synchronizes with the core server 160, the first processor 220 becomes aware of the third flag. The first processor 220 then receives the request for access to the de-identified data on sending the identification hash to the core server 160. Further, the first processor 220 then is enabled to transmit the record identification to the core server 160 in response to the request.

Further, the core server 160 is configured to receive the record identification from the first client device 110*a* in response to the request and transmit the record identification to the research database 195. Further, the core server 160 is configured to generate a research record hash and transmit the research record hash to the research database 195 to be stored in association with the record identification. Further, the core server 160 is configured to transmit the research record hash to the third client device 110*c*.

When the researches wishes to access the de-identified data, the researcher may use the research record hash from the third client device. In one embodiment of the invention, the third computer program code further enables the third processor 620 to query the core server 160 using the research record hash for viewing of the de-identified data. Further, the core server 160 is configured to receive the research record hash from the third client device 110*c*. On receiving the research record hash from the third client device 110*c*, the core server 160 then is configured to query the research database 195 using the research record hash and receive the record identification from the research database 195. Further the core server 160 is configured to query the repository database 170 using the record identification and receive the de-identified data at the core server 160 from the repository database 170.

Further, the core server 160 is configured to provide a second viewing medium to the third client device 110*c*. Further, the second viewing medium is configured for viewing of the de-identified data at the third client device 110*c*. The third processor 620, in turn is enabled to receive the second viewing medium from the core server 160. It is to be noted that de-identified data is not transmitted to the third client device 110*c* and only the second viewing medium, such as a URL is provided. The URL may remain valid temporarily or permanently. This feature is to ensure that the confidentiality of the de-identified data is maintained and that the de-identified data is not misused by the researcher.

Computing Device

Figure 7:
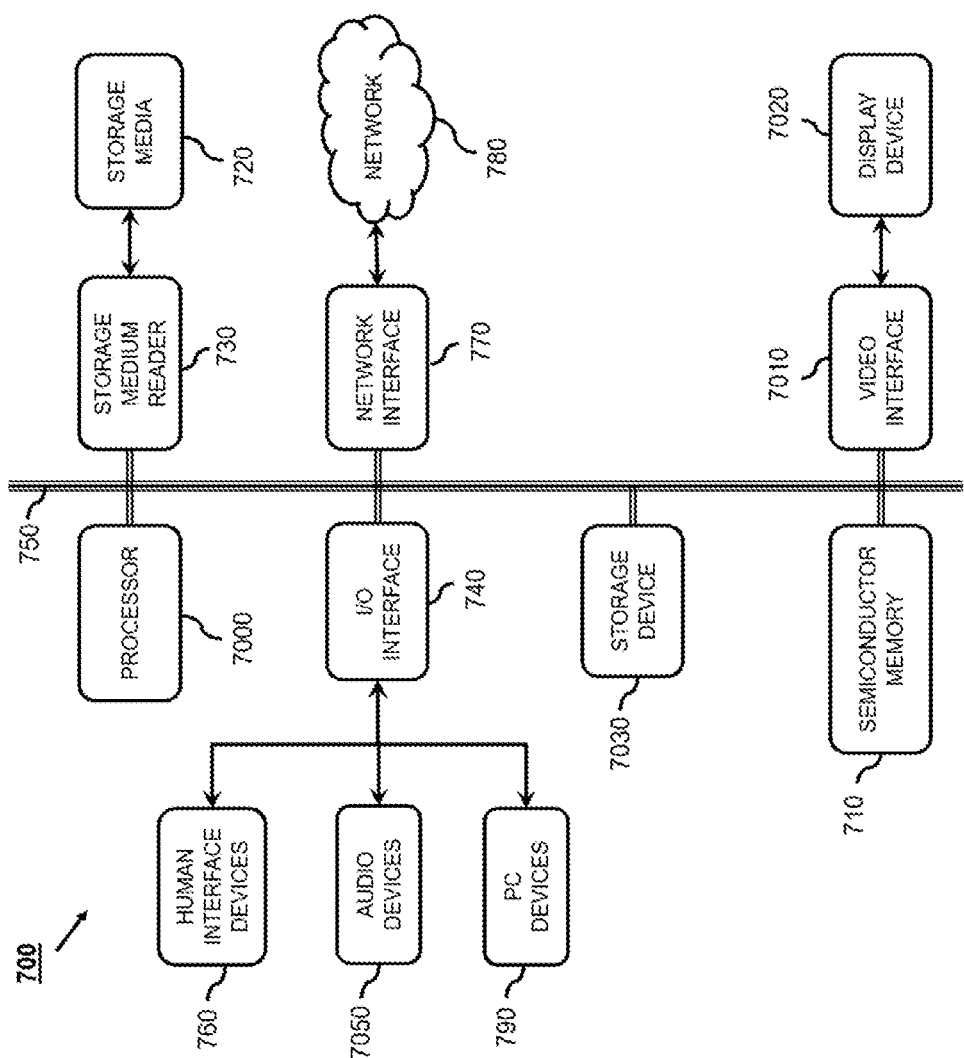
FIG. 7 illustrates a computing device to which various embodiments described herein may be implemented.

FIG. 7 shows a computing device 700. In a preferred embodiment, the computing device 700 takes the form of the API server 150, the HSP server 130, the core server 160 and the claims authorization server 190 as described above. In this manner, the computing device 700 is adapted to comprise functionality for communication with the network 120, storage capability (such as the medical database 140) for storing the data corresponding to the plurality of users.

However, it should be noted that each one of the plurality of client devices 110, as shown in FIG. 1, may also be depicted as the computing device 700. In this manner, the computing device may comprise differing technical integers, such as the display device 7020, one or more human interface devices 760 and the like. In other words, the technical integers of the computing device 700 is shown in FIG. 7 are exemplary only and variations, adaptations and the like may be made thereto within the purposive scope of the embodiments described herein and having regard for the particular application of the computing device 800.

In particular the steps of the computer implemented method for secure management of data generated in an EHR during an episode of care, as described in further detail below, may be implemented as computer program code instructions executable by the computing device 700. The computer program code instructions may be divided into one or more computer program code instruction libraries, such as dynamic link libraries (DLL), wherein each of the libraries performs a one or more steps of the computer implemented method. Additionally, a subset of the one or more of the libraries may perform graphical user interface tasks relating to the steps of the computer implemented method.

The device 700 comprises semiconductor memory 710 comprising volatile memory such as random access memory (RAM) or read only memory (ROM). The memory 700 may comprise either RAM or ROM or a combination of RAM and ROM.

The device 700 comprises a computer program code storage medium reader 730 for reading the computer program code instructions from computer program code storage media 720. The storage media 720 may be optical media such as CD-ROM disks, magnetic media such as floppy disks and tape cassettes or flash media such as USB memory sticks.

The device further comprises I/O interface 740 for communicating with one or more peripheral devices. The I/O interface 740 may offer both serial and parallel interface connectivity. For example, the I/O interface 740 may comprise a Small Computer System Interface (SCSI), Universal Serial Bus (USB) or similar I/O interface for interfacing with the storage medium reader 730. The I/O interface 740 may also communicate with the one or more human interface devices (HID) 760 such as keyboards, pointing devices, joysticks and the like. The I/O interface 740 may also comprise a computer to computer interface, such as a Recommended Standard 232 (RS-232) interface, for interfacing the device 700 with one or more personal computer (PC) devices 790. The I/O interface 740 may also comprise an audio interface for communicate audio signals to one or more audio devices 7050, such as a speaker or a buzzer.

The device 700 also comprises a network interface 770 for communicating with one or more computer networks 780. The network 780 may be a wired network, such as a wired Ethernet™ network or a wireless network, such as a Bluetooth™ network or IEEE 802.11 network. The network 780 may be a local area network (LAN), such as a home or office computer network, or a wide area network (WAN), such as the Internet or private WAN.

The device 700 comprises an arithmetic logic unit or processor 7000 for performing the computer program code instructions. The processor 7000 may be a reduced instruction set computer (RISC) or complex instruction set computer (CISC) processor or the like. The device 800 further comprises a storage device 7030, such as a magnetic disk hard drive or a solid state disk drive.

Computer program code instructions may be loaded into the storage device 7030 from the storage media 720 using the storage medium reader 730 or from the network 780 using network interface 770. During the bootstrap phase, an operating system and one or more software applications are loaded from the storage device 7030 into the memory 710. During the fetch-decode-execute cycle, the processor 7000 fetches computer program code instructions from memory 710, decodes the instructions into machine code, executes the instructions and stores one or more intermediate results in memory 700.

In this manner, the instructions stored in the memory 710, when retrieved and executed by the processor 7000, may configure the computing device 700 as a special-purpose machine that may perform the functions described herein.

The device 700 also comprises a video interface 7010 for conveying video signals to a display device 7020, such as a liquid crystal display (LCD), cathode-ray tube (CRT) or similar display device.

The device 700 also comprises a communication bus subsystem 750 for interconnecting the various devices described above. The bus subsystem 850 may offer parallel connectivity such as Industry Standard Architecture (ISA), conventional Peripheral Component Interconnect (PCI) and the like or serial connectivity such as PCI Express (PCIe), Serial Advanced Technology Attachment (Serial ATA) and the like.

De-Identification of Data and Record Generation

Figure 8:
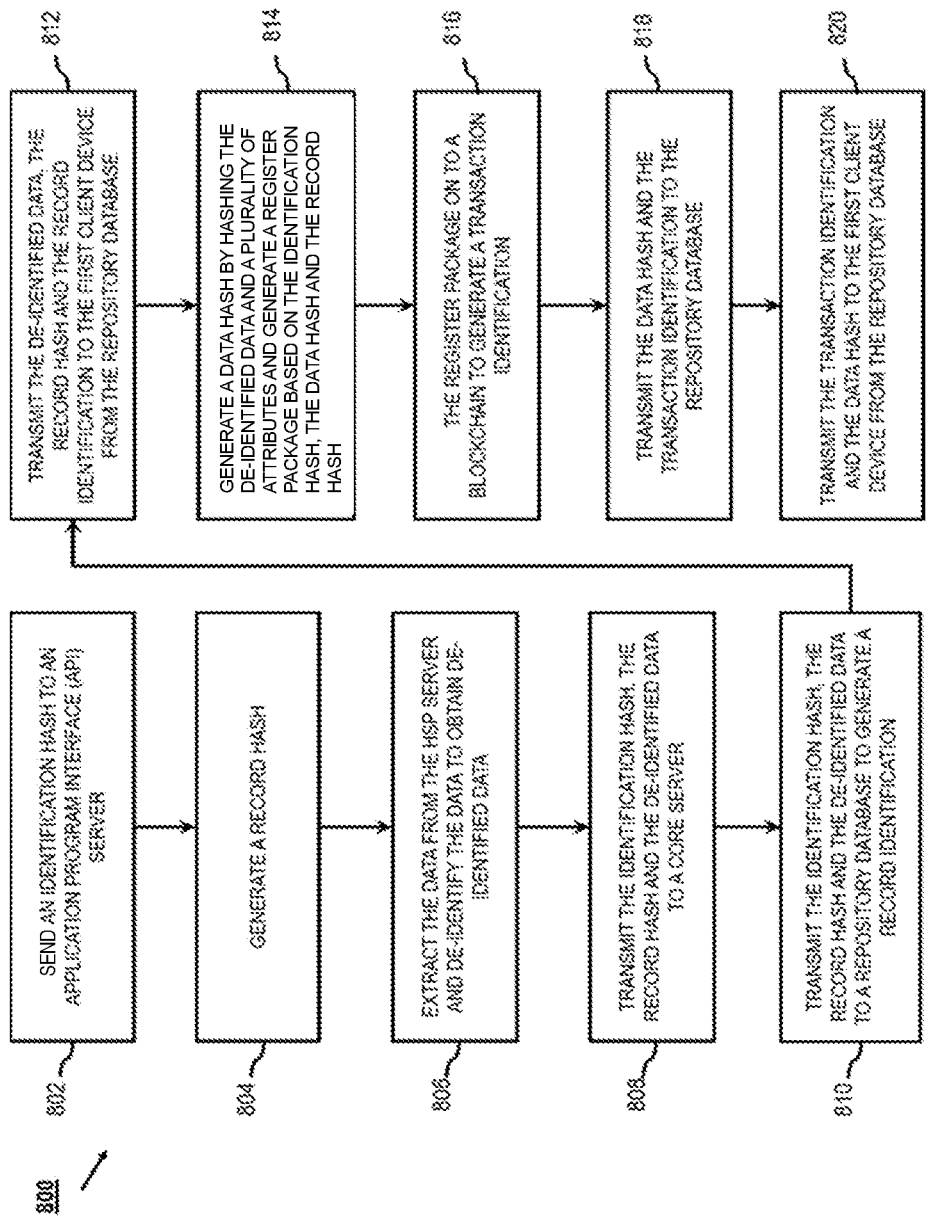
FIG. 8 illustrates a computer implemented method for secure management of data generated in an EHR during an episode of care, in accordance with a preferred embodiment of the present invention.

FIG. 8 illustrates a method 800 for secure management of data generated in an EHR, during an episode of care, for a user. The computer implemented method begins at step 802, by sending an identification hash from the first client device 110*a* to the API server 150. The identification hash is a unique hash corresponding to the first client device 110*a*. In one embodiment of the invention, the identification hash is sent to the first client device 110*a* through the first computer program code. Alternately, the identification hash is generated by the first client device 110*a*.

Figure 9:
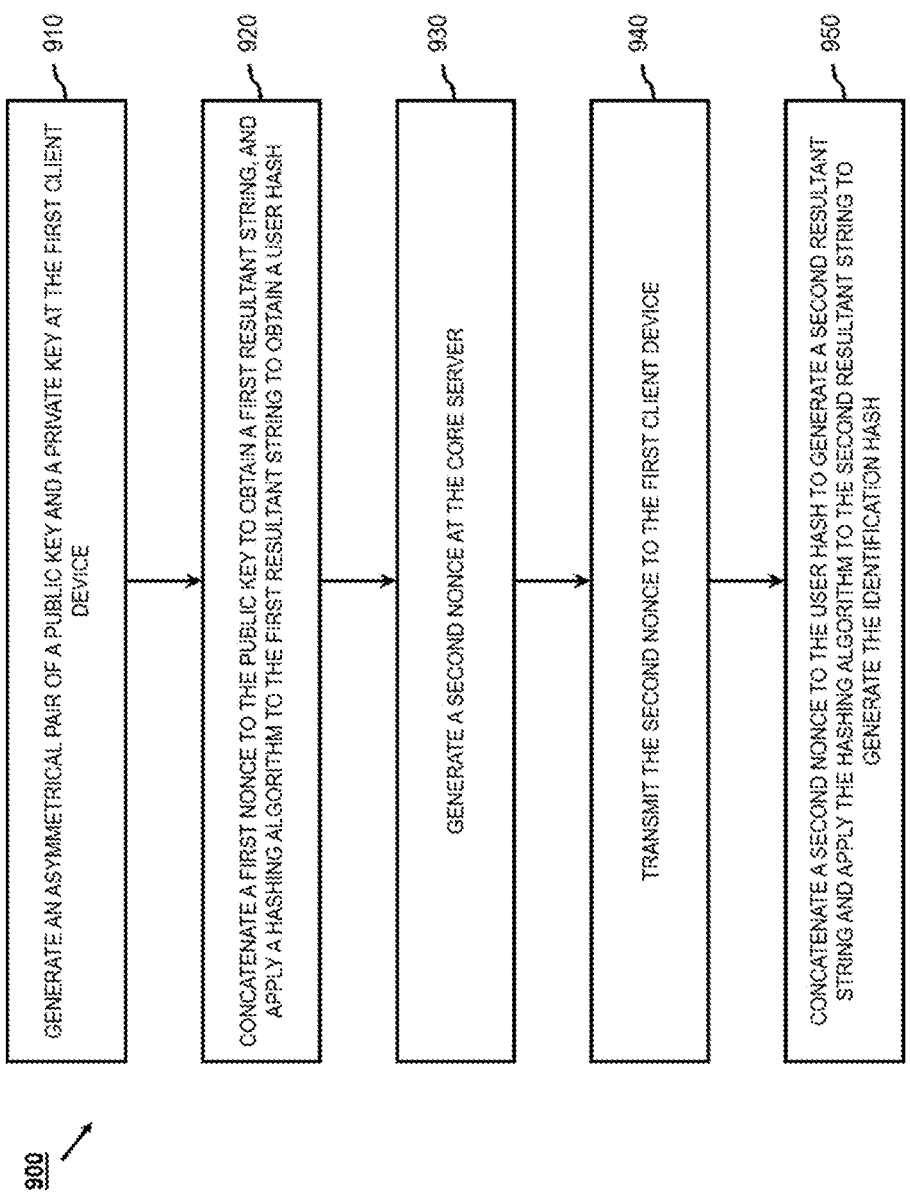
FIG. 9 illustrates a computer implemented method for generation of the identification hash at the core server, in accordance with a preferred embodiment of the present invention.

FIG. 9 illustrates a method 900 for generation of the identification hash at the first client device 110*a*. At step 910, an asymmetrical pair of a public key and a private key is generated by the first processor 220 at the first client device 110*a*. In one embodiment of the invention, the asymmetrical pair of the public key and the private key is generated from Elliptical Curve Digital Signature (ECDS) algorithm. Further, the private key is stored in a secure area at the first client device. Storing the private key inside a secure area provides a layer of hardware protection for the private key.

At step 920, a first nonce is concatenated to the public key to generate a first resultant string and a hashing algorithm is applied to the first resultant string to obtain a user hash, by the first processor 220, at the first client device 110*a*. The first nonce is generated to have a high entropy characteristic. In one embodiment of the invention the hashing algorithm is, but not limited to, SHA256. At step 930, a second nonce corresponding to the user hash is generated at the core server 160. At step 940, the second nonce is transmitted to the first client device 110*a* from the core server 160.

At step 950, the second nonce is concatenated to the user hash to generate a second resultant string by the first processor 220. Further, the hashing algorithm is applied to the second resultant string to generate the identification hash at the first client device 110*a*. It is to be noted that no record of the second nonce is maintained at the core server 160. The deletion of the second nonce ensures that, in case the core server 160 is hacked, the second nonce will not be stolen from the core server 160. Further, deletion of the second nonce also constitutes to good housekeeping, and thus storage space at the core server 160 is not wasted.

Returning now to FIG. 8 and the consequent discussion, in one embodiment of the invention, the identification hash is sent to the API server 150 through a first offline communication medium. Further, the first offline communication medium is selected from a group of technologies that are able to carry the identification hash, including but not limited to, Quick Response (QR) code, Near Field Communication (NFC) and Bluetooth. The use of the first offline communication medium ensures that the identity of the first client device 110*a* is not disclosed to the API server 150. In one embodiment of the invention, one or more first details corresponding to the user, are displayed by the first processor 220, at the first client device 110a, to allow verification of an identity of the user. The one or more first details include, but are not limited to, name, age, biometric data and sex of the user. In one embodiment of the invention, the identity of the user is verified by a receptionist available with the API server 150. In accordance with another embodiment, the API server 150 comprises an in-built module for verification of the identity of the user. In one embodiment of the invention, on receiving the identification hash, the API server 150 stores the identification hash in association with the identity of the user, at an API server memory provided at the API server 150.

At step 804, a record hash is generated at the API server 150. The record hash corresponds to a record being generated during an instance of carrying out of the computer implemented method 800.

At step 806, the data is extracted from the HSP server 130 and the data is de-identified to obtain de-identified data at the API server 150. In one embodiment of the invention, the API server prompts the HSP server 130 for the data, with the one or more first details of the user. The HSP server 130 then queries the medical database 140 for the data. On receiving the data from the medical database 140, the HSP server 130 transmits the data to the API server 150. In one embodiment of the invention, de-identifying data includes removal of all the fields from the data, which may lead to identification of the user by a system, a device or any other person.

At step 808, the identification hash, the record hash and the de-identified data are transmitted from the API server 150 to the core server 160. At step 810, the core server 160 receives the de-identified data, the record hash and the identification hash from the API server 150 and transmits the de-identified data, the record hash and the identification hash to the repository database 170 to generate a record identification. At step 812, the de-identified data, the record hash and the record identification is transmitted from the repository database 170 to the first client device 110a, via the core server 160. It is to be noted that the de-identified data, the record hash and the record identification are not "pushed" to the first client device 110a. In other words, the de-identified data, the record hash and the record identification is not immediately transmitted to the first client device 110a. It is an important security feature, as it will discourage any hacker to steal the de-identified data, the record hash and the record identification through attacks such as MITM attacks. In one embodiment of the invention, a first flag is set at the core server 160 corresponding to the identification hash.

The first processor 220 synchronizes with the core server 160. In one embodiment of the invention, the first processor 220 synchronizes with the core server 160 during an event of initiation of execution of the first computer program code. In accordance with another embodiment, the first processor 220 synchronizes with the core server 160 periodically. When the first processor 220 becomes aware of the first flag, the first processor 220 can receive (or "pull") the de-identified data, the record hash and the record identification from the repository database 170. In one embodiment of the invention, the de-identified data, the record hash and the record identification is transmitted to the first client device 110a in response to receiving of the identification hash from the first client device 110a at the core server 160. The core server 160 then queries the repository database 170 using the identification hash and receives the de-identified data, the record hash and the record identification from the repository database 170. The core server 160 then transmits the de-identified data, the record hash and the record identification to the first client device 110a. The first processor 220 then receives the de-identified data, the record hash and the record identification from the core server 160.

Further, in one embodiment of the invention, the core server 160 further verifies the de-identified data with the first client device 110a after transmitting the de-identified data to the first client device 110a. In one embodiment of the invention, the de-identified data is displayed to the user for verification. In accordance with another embodiment, the de-identified data is verified automatically by the first processor 220 through execution of the first computer program code.

In one embodiment of the invention, the first processor 220 transmits the identification hash and the record hash to the core server 160. The core server 160 then queries the repository database 170 using the identification hash and the record hash. The core server 160 then receives the de-identified data from the repository database 170, in response to the query. At step 814, a data hash is generated by hashing the de-identified data and plurality of attributes corresponding to the de-identified data, at the core server 160. In one embodiment of the invention, the plurality of attributes comprise a geographical location tag and a time stamp. In accordance with another embodiments, the plurality of attributes comprise SNOMED codes and LOINC codes corresponding to the de-identified data. Further, a register package is generated at the core server 160 based on (for example by fusing) the identification hash, the record hash and the data hash.

At step 816, the register package is stored (by for example mining) on to the blockchain 180, from the core server 160, to generate a transaction identification. In one embodiment of the invention, the core server 160 further verifies the register package with the first client device 110a before storing the register package on to the blockchain 180. In accordance with the embodiment, the first processor 220 regenerates the identification hash from the private key using the ECDS algorithm, the first nonce, the second nonce and the hashing algorithm. Further, the first processor 220 transmits the identification hash to the core server 160. The core server 160 then uses the identification hash received from the first client device 110a to generate a second instance of the register package. If the second instance of the register package matches the register package generated at the core server 160, the register package is verified.

The blockchain 180 generates the transaction identification on receiving the register package. The blockchain 180 is configured to return the register package, when queried by any of the computing devices of system 100, using the transaction identification. At step 818, the data hash and the transaction identification are transmitted from the core server 160 to the repository database 170. At step 820 the transaction identification and the data hash are transmitted to the first client device 110a from the repository database 170, via the core server 160. In one embodiment of the invention, a second flag is set at the core server 160 corresponding to the identification hash.

The first processor 220 then synchronizes with the core server 160. In one embodiment of the invention, the first processor 220 synchronizes with the core server 160 during an event of initiation of execution of the first computer program code. In accordance with another embodiment, the first processor 220 synchronizes with the core server 160 periodically. When the first processor 220 becomes aware of the second flag, the first processor 220 can receive (or "pull") the transaction identification and the data hash from the repository database 170.

In one embodiment of the invention, the first processor 220 receives the transaction identification and the data hash in response to sending the identification hash to the core server 160. The core server 160 queries the repository database 170 using the identification hash and receives the transaction identification and the data hash from the repository database 170. The core server 160 then transmits the transaction identification and the data hash to the first client device 110*a*. The first processor 220 then receives the transaction identification and the data hash from the core server 160.

It is to be noted that no record of the transaction identification and the data hash is kept at the core server 160 for security of the transaction identification and the data hash.

Further, first processor 220 receives the transaction identification and the data hash from the core server 160 and stores the transaction identification and the data hash in the first memory 210. In one embodiment of the invention, the first processor 220 regenerates the register package based on the identification hash, the record hash and the data hash. Further, the first processor 220 verifies the register package with the blockchain 180, using the transaction identification. In one embodiment of the invention, the first processor 220 verifies the register package using a plurality of blockchain utilities.

Claims Authorization

Figure 10:
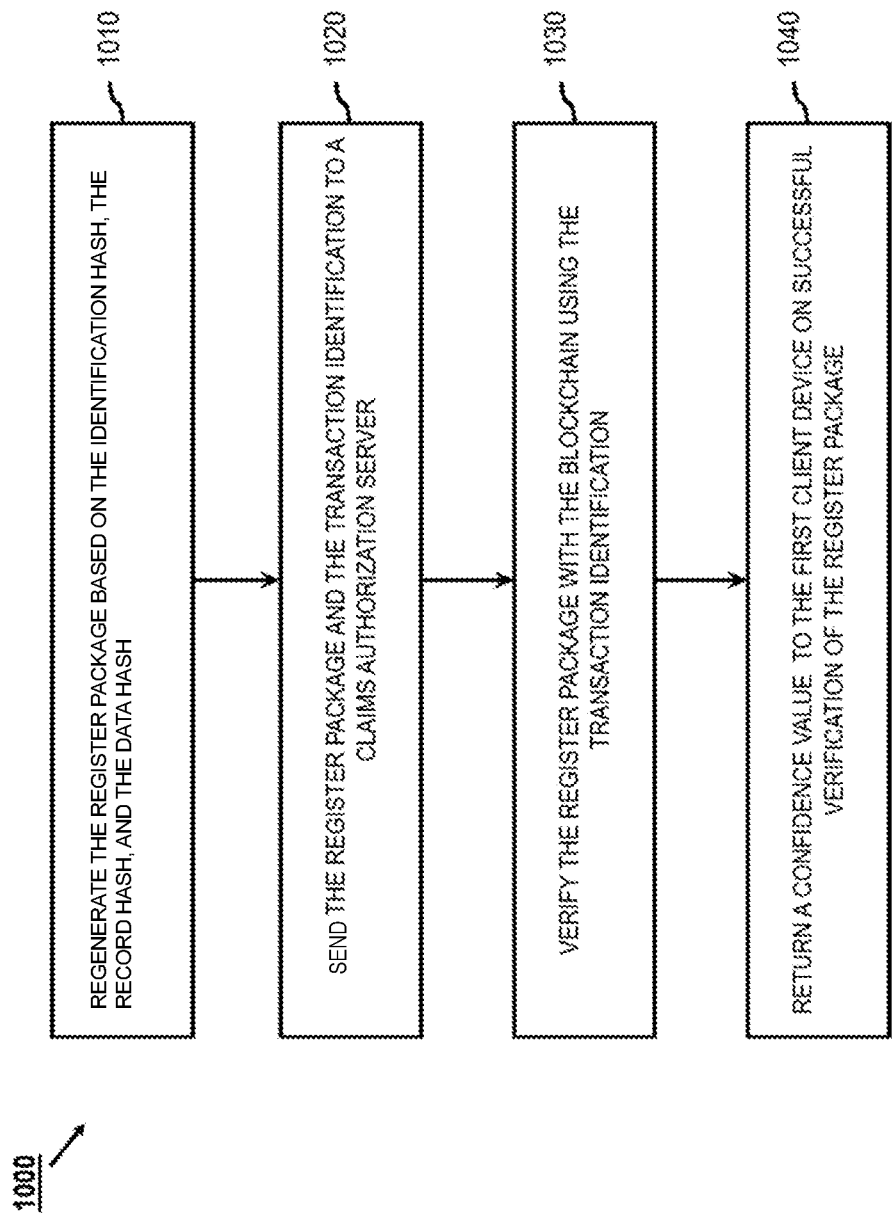
FIG. 10 illustrates a computer implemented method for the authorization of the insurance claim using the claims authorization server in accordance with a preferred embodiment of the present invention.

FIG. 10 illustrates a method (1000) for authorization of an insurance claim for the episode of care with the claims authorization server 190. The computer implemented method, at step 1010, regenerates the register package at the first client device 110*a* by the first processor 220 based on the identification hash, the record hash and the data hash. At step, 1020 the register package and the transaction identification are sent to the claims authorization server 190, by the first processor 190. At step 1030, the claims authorization server 190 verifies the register package with the blockchain 180, using the transaction identification. At step 1040, the claims authorization server 190, returns a confidence value to the first client device 110*a*, on verification of the register package. If the confidence value is greater than a predetermined threshold, the insurance claim is authorized.

Sharing of De-Identified Data

Figure 11:
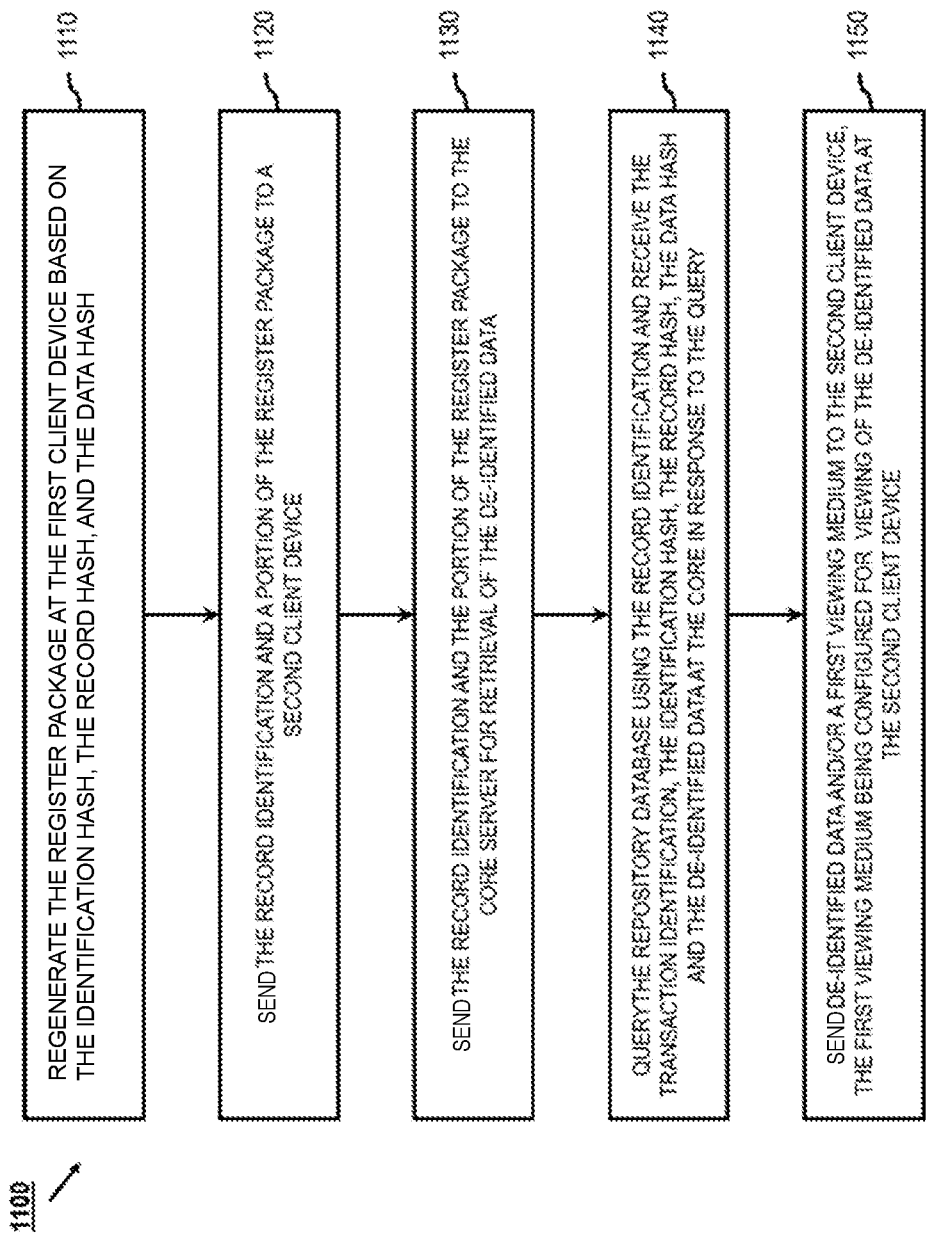
FIG. 11 illustrates a computer implemented method for viewing of the de-identified data at the second client device, in accordance with a preferred embodiment of the present invention.

The de-identified data may be anonymously shared with a pharmacist or a clinician. FIG. 11 illustrates a method (1100) for sharing of de-identified data with the clinician or the pharmacist, at the second client device 110*b*, in one embodiment of the invention. The computer implemented method, at step 1110, regenerates the register package at the first client device 110*a*, by the first processor 220 based on the identification hash, the record hash and the data hash. At step 1120, the record identification and a portion of the register package is sent to the second client device 110*b*, by the first processor 220.

In one embodiment of the invention, the portion of the register package and the record identification are sent to the second client device 110*b* through a second offline communication medium. Further, in one embodiment of the invention, the second offline communication medium is selected from a group of technologies that are able to carry the portion of the register package and the record identification, including but not limited to, Quick Response (QR) code, Near Field Communication (NFC) and Bluetooth. The use of the second offline communication medium ensures that the identity of the first client device 110*a* is not disclosed to the second client device 110*b*. Further, the first processor 220 provides one or more second details corresponding to the user for verification of an identity of the user. In one embodiment of the invention, the one or more second details comprise, but are not limited to, name, age, sex, biometric data and address of the user. In one embodiment of the invention, the one or more second details are displayed to the second user at the first client device 110*a*. In accordance with another embodiment, the one or more second details are transmitted to the second client device 110*b* through the second offline communication medium.

At step 1130, the second processor 520 sends the record identification and the portion of the register package to the core server 160 for retrieval of the de-identified data. The core server 160 then receives the record identification and the portion of the register package from the second client device 110*b*. At step 1140, the core server 160 queries the repository database 170 using the record identification and the portion of the register package and receives the transaction identification, the identification hash, the record hash, the data hash and the de-identified data from the repository database 170 in response to the query. In one embodiment of the invention, the core server 160 further regenerates the register package based on the identification hash, the record hash and the data hash. Further, the core server 160 verifies the regenerated register package with the portion of the register package received from the second client device 110*b*.

At step 1150, the core server 160 sends at least one of the de-identified data and a first viewing medium to the second client device 110*b*, the first viewing medium being configured for viewing of the de-identified data at the second client device. In one embodiment of the invention, size of the de-identified data is not large and the de-identified data is sent to the second client device 110*b*. In another embodiment, the de-identified data is sent partly and rest of the part of the de-identified is sent through the first viewing medium. In one embodiment of the invention, the first viewing medium is a first URL. Further, the first URL may be have a temporary validity or a permanent validity. In one embodiment of the invention, the core server 160 further transmits the register package and the transaction identification to the second client device 110*b*. Further, the second processor 520 receives the register package and the transaction identification from the core server 160. Also the second processor 520, further verifies the register package with the blockchain 180 using the transaction identification.

Figure 12:
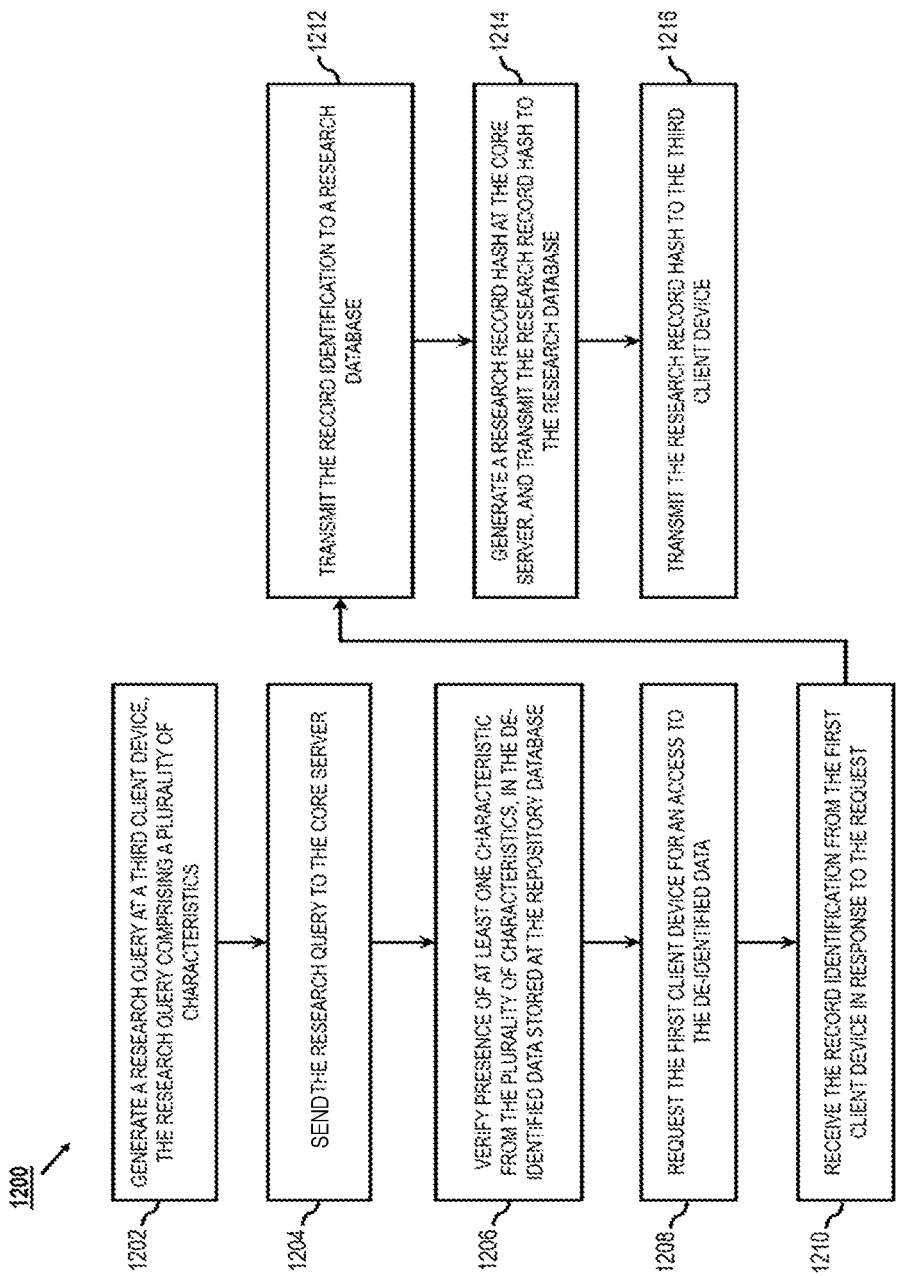
FIG. 12 illustrates a computer implemented method for generation of a research record, in accordance with a preferred embodiment of the present invention.

A researcher may be interested in analysing the de-identified data. Consequently, the researcher should be able to generate a research record in the research database 195, linking the researcher to the de-identified data stored in the repository database 170. FIG. 12 illustrates a method 1200 for generation of a research record by the researcher using the third client device 110*c*. The computer implemented method begins at step 1202, by generating a research query at the third client device 110*c*, by the third processor 620. The research query is such that, it comprises a plurality of characteristics. In one embodiment of the invention, the plurality of characteristics comprise filter data such as, but not limited to, a general interest, a medical disease, gender, geographical region and time period etc.

At step 1204, the research query is sent by the third processor 620, to the core server 160. In one embodiment of the invention, the research query is sent to the core server 160 in a form of a search string at a research portal. At step 1206, the core server 160 verifies of a presence of at least one characteristic from the plurality of characteristics, in the de-identified data stored at the repository database 170. At step 1208, on verification of the presence of the at least one characteristic, the core server 160 requests the first client device for an access to the de-identified data. In accordance with an embodiment, a third flag is set in at the core server 160, corresponding to the identification hash. When the first processor 220 synchronizes with the core server 160, the first processor 220 becomes aware of the third flag. The first processor 220 then receives the request for access to the de-identified data on sending the identification hash to the core server 160. Further, the first processor 220 then transmits the record identification to the core server 160 in response to the request.

At step 1210, the record identification is received at the core server 160 in response to the request. At step 1212, the core server 160 transmits the record identification to the research database 195, creating a new entry in the research database 195. The record identification stored in the research database 195 acts as the link to the de-identified data stored in the repository database 170. At step 1214, the core server 160 generates a research record hash and transmits the research record hash to the research database 195 to be stored in association with the record identification. At step 1216, the core server 160 transmits the research record hash to the third client device 110c.

Figure 13:
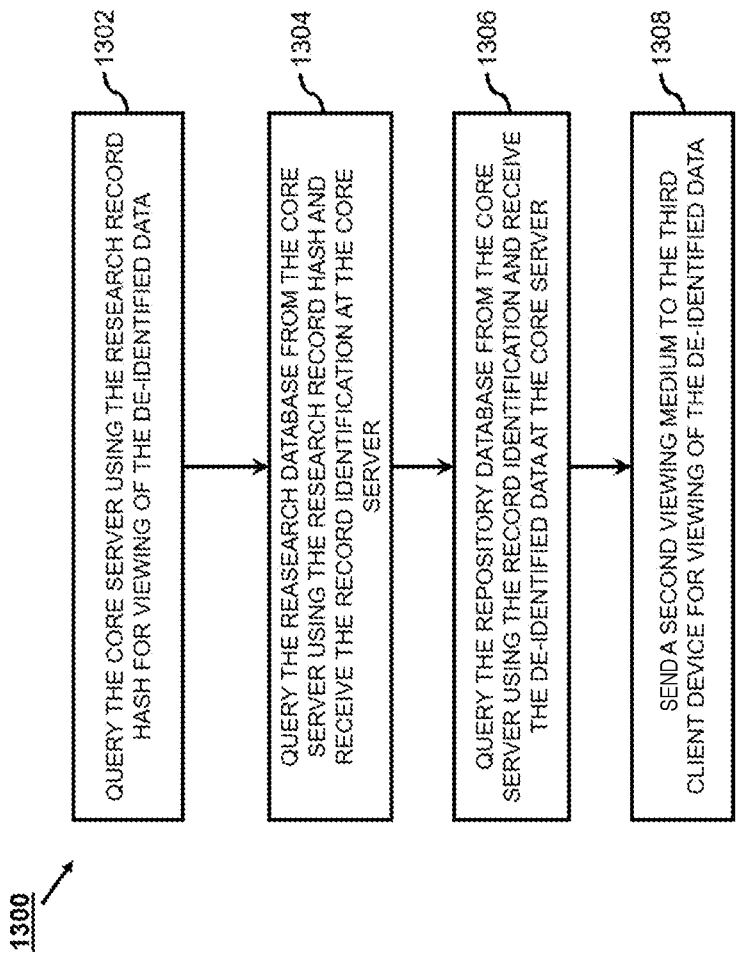
FIG. 13 illustrates a computer implemented method for viewing of the de-identified data by the researcher using the third client device, in accordance with a preferred embodiment of the present invention.

In one embodiment of the present invention, the researcher wishes to view the de-identified data at the third client device 110c. The researcher is able to view the de-identified data at the third client device 110c by sending the research record hash to the core server 160 from the third client device 110c. FIG. 13 illustrates a method 1300 for viewing of the de-identified data at the third client device. At step 1302, the first processor 620 queries the core server 160 using the research record hash. The core server 160 receives the research record hash from the third client device 110c. At step 1304, the core server 160 queries the research database 195 using the research record hash and receives the record identification from the research database 195.

At step 1306, the core server queries the repository database 170 using the record identification and receives the de-identified data from the repository database 170. At step 1308, the core server 160 sends a second viewing medium to the third client device 110c, the second viewing medium being configured for viewing of the de-identified data at the third client device 110c. In one embodiment of the invention, the second viewing medium is a temporary or a permanent URL.

The system and the computer implemented methods described above offer a plurality of advantages over existing system and methods. First, the identification details of the user are not stored on either of the core server 160 and/or the repository database 170. Therefore, in a scenario, where the core server 160 and/or the repository database 170 are hacked, there will be no way of linking the de-identified data back to the user. Because EHR details can be verified using the register package on the blockchain 180, no trusted centralized register of the user needs to exist. No central "reverse look up" table exists.

Further, the use of hashes facilitates one way encryption of various parameters associated with the user and the de-identified data. There is very minimal likelihood that a hacker may be able to guess or determine by other means, the starting strings used for generation of the hashes. Further, the hashes are so designed, that any alteration in any of the starting strings will lead to a drastically different output from the hashing algorithm. Therefore, any tampering of the starting strings, such as a geographical location tag or a time stamp, will lead to an erroneous data hash and consequently an erroneous register package. This feature is highly beneficial, when the user is to be prevented from making false insurance claims.

Further, the invention provides benefits of integrating various formats of EHRs such as FHIR and HL7, and codification schemes such as LOINC and SNOMED codes. The invention further facilitates sharing of data, in a secure way with a clinician for seeking advice. Also the invention allows provisioning of a research portal, where the de-identified data can be used by a researcher for studying a disease, plotting epidemiological patterns and conducting surveys.

Interpretation

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein. For the purposes of the present invention, additional terms are defined below. Furthermore, all definitions, as defined and used herein, should be understood to control over dictionary definitions, definitions in documents incorporated by reference, and/or ordinary meanings of the defined terms unless there is doubt as to the meaning of a particular term, in which case the common dictionary definition and/or common usage of the term will prevail.

The terminology used herein is for the purpose of describing particular embodiments only and is not intended to be limiting of the invention. As used herein, the singular articles "a", "an" and "the" are intended to include the plural forms as well, unless the context clearly indicates otherwise and thus are used herein to refer to one or to more than one (i.e. to "at least one") of the grammatical object of the article. By way of example, the phrase "an element" refers to one element or more than one element.

The term "about" is used herein to refer to quantities that vary by as much as 30%, preferably by as much as 20%, and more preferably by as much as 10% to a reference quantity. The use of the word 'about' to qualify a number is merely an express indication that the number is not to be construed as a precise value.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The term "real-time" for example "displaying real-time data," refers to the display of the data without intentional delay, given the processing limitations of the system and the time required to accurately measure the data.

As used herein, the term "exemplary" is used in the sense of providing examples, as opposed to indicating quality. That is, an "exemplary embodiment" is an embodiment provided as an example, as opposed to necessarily being an embodiment of exemplary quality for example serving as a desirable model or representing the best of its kind.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, In one embodiment of the invention, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, In one embodiment of the invention, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Bus

In the context of this document, the term "bus" and its derivatives, while being described in a preferred embodiment as being a communication bus subsystem for interconnecting various devices including by way of parallel connectivity such as Industry Standard Architecture (ISA), conventional Peripheral Component Interconnect (PCI) and the like or serial connectivity such as PCI Express (PCIe), Serial Advanced Technology Attachment (Serial ATA) and the like, should be construed broadly herein as any system for communicating data.

In accordance with:

As described herein, 'in accordance with' may also mean 'as a function of' and is not necessarily limited to the integers specified in relation thereto.

Composite Items

As described herein, 'a computer implemented method' should not necessarily be inferred as being performed by a single computing device such that the steps of the computer implemented method may be performed by more than one cooperating computing devices.

Similarly objects as used herein such as 'web server', 'server', 'client computing device', 'computer readable medium' and the like should not necessarily be construed as being a single object, and may be implemented as a two or more objects in cooperation, such as, for example, a web server being construed as two or more web servers in a server farm cooperating to achieve a desired goal or a computer readable medium being distributed in a composite manner, such as program code being provided on a compact disk activatable by a license key downloadable from a computer network.

Database:

In the context of this document, the term "database" and its derivatives may be used to describe a single database, a set of databases, a system of databases or the like. The system of databases may comprise a set of databases wherein the set of databases may be stored on a single implementation or span across multiple implementations. The term "database" is also not limited to refer to a certain database format rather may refer to any database format. For example, database formats may include MySQL, MySQLi, XML or the like.

Wireless:

The invention may be embodied using devices conforming to other network standards and for other applications, including, for example other WLAN standards and other wireless standards. Applications that can be accommodated include IEEE 802.11 wireless LANs and links, and wireless Ethernet.

In the context of this document, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In the context of this document, the term "wired" and its derivatives may be used to describe circuits, devices, systems, methods, techniques, communications channels, etc., that may communicate data through the use of modulated electromagnetic radiation through a solid medium. The term does not imply that the associated devices are coupled by electrically conductive wires.

Processes:

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

Processor:

In a similar manner, the term "processor" may refer to any device or portion of a device that processes electronic data, e.g., from registers and/or memory to transform that electronic data into other electronic data that, e.g., may be stored in registers and/or memory. A "computer" or a "computing device" or a "computing machine" or a "computing platform" may include one or more processors.

The computer implemented methodologies described herein are, In one embodiment of the invention, performable by one or more processors that accept computer-readable (also called machine-readable) code containing a set of instructions that when executed by one or more of the processors carry out at least one of the computer implemented methods described herein. Any processor capable of executing a set of instructions (sequential or otherwise) that specify actions to be taken are included. Thus, one example is a typical processing system that includes one or more processors. The processing system further may include a memory subsystem including main RAM and/or a static RAM, and/or ROM.

Computer-Readable Medium:

Furthermore, a computer-readable carrier medium may form, or be included in a computer program product. A computer program product can be stored on a computer usable carrier medium, the computer program product comprising a computer readable program means for causing a processor to perform a method as described herein.

Networked or Multiple Processors:

In alternative embodiments, the one or more processors operate as a standalone device or may be connected, e.g., networked to other processor(s), in a networked deployment, the one or more processors may operate in the capacity of a server or a client machine in server-client network environment, or as a peer machine in a peer-to-peer or distributed network environment. The one or more processors may form a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the computer implemented methodologies discussed herein.

ADDITIONAL EMBODIMENTS

Thus, one embodiment of each of the computer implemented methods described herein is in the form of a computer-readable carrier medium carrying a set of instructions, e.g., a computer program that are for execution on one or more processors. Thus, as will be appreciated by those skilled in the art, embodiments of the present invention may be embodied as a method, an apparatus such as a special purpose apparatus, an apparatus such as a data processing system, or a computer-readable carrier medium. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

Carrier Medium:

The software may further be transmitted or received over a network via a network interface device. While the carrier medium is shown in an example embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the computer implemented methodologies of the present invention. A carrier medium may take many forms, including but not limited to, non-volatile media, volatile media, and transmission media.

Implementation:

It will be understood that the steps of methods discussed are performed In one embodiment of the invention by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Means for Carrying Out a Method or Function

Furthermore, some of the embodiments are described herein as a method or combination of elements of a method that can be implemented by a processor of a processor device, computer system, or by other means of carrying out the function. Thus, a processor with the necessary instructions for carrying out such a method or element of a method forms a means for carrying out the computer implemented method or element of a method. Furthermore, an element described herein of an apparatus embodiment is an example of a means for carrying out the function performed by the element for the purpose of carrying out the invention.

Connected

Similarly, it is to be noticed that the term connected, when used in the claims, should not be interpreted as being limitative to direct connections only. Thus, the scope of the expression a device A connected to a device B should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other.

EMBODIMENTS

Reference throughout this specification to "one embodiment" or "an embodiment" means that a particular feature, structure or characteristic described in connection with the embodiment is included in at least one embodiment of the present invention. Thus, appearances of the phrases "In one embodiment of the invention" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

It will be appreciated that the computer implemented methods and systems described/illustrated above at least substantially provides a manner in which data generated in an EHR, during an episode of care, may be de-identified (or anonymized) and provided to a user through a secure channel.

The embodiments described herein, and/or shown in the drawings, are presented by way of example only and are not limiting as to the scope of the invention. Unless otherwise specifically stated, individual aspects and components of the embodiments may be modified, or may have been substituted therefore known equivalents, or as yet unknown substitutes such as may be developed in the future or such as may be found to be acceptable substitutes in the future. The embodiments may also be modified for a variety of applications while remaining within the scope and spirit of the claimed invention, since the range of potential applications is great, and since it is intended that the present invention be adaptable to many such variations.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

Chronological Order

For the purpose of this specification, where method steps are described in sequence, the sequence does not necessarily mean that the steps are to be carried out in chronological order in that sequence, unless there is no other logical manner of interpreting the sequence.

INDUSTRIAL APPLICABILITY

It is apparent from the above, that the arrangements described are applicable to the industries dealing with healthcare, medical insurance, medical research and pharmaceuticals etc.

The invention claimed is:

1. A computer implemented method for secure management of data generated in an Electronic Health Record (EHR) during an episode of care, for a user, wherein the EHR is being maintained in a medical database comprised within a Healthcare Service Provider (HSP) server, the computer implemented method comprising the steps of:
   sending an identification hash corresponding to the user to an Application Program Interface (API) server from a first client device;
   extracting the data from the HSP server and de-identifying the data to obtain de-identified data at the API server;
   generating a record hash at the API server;
   transmitting the identification hash, the record hash and the de-identified data from the API server to a core server;
   receiving the identification hash, the record hash and the de-identified data at the core server and transmitting the identification hash, the record hash and the de-identified data from the core server to a repository database to generate a record identification;
   transmitting the de-identified data, the record hash and the record identification from the repository database to the first client device, via the core server;
   generating a data hash by hashing the de-identified data and a plurality of attributes corresponding to the de-identified data;

generating at the core server a register package based on the data hash, the identification hash and the record hash;

storing the register package, from the core server, on to a blockchain to generate a transaction identification;

transmitting the data hash and the transaction identification from the core server to the repository database; and transmitting the transaction identification and the data hash from the repository database to the first client device, via the core server.

2. The computer implemented method as claimed in claim 1, further comprising the steps of:

generating an asymmetrical pair of a public key and a private key at the first client device;

concatenating a first nonce to the public key to obtain a first resultant string, and applying a hashing algorithm to the first resultant string to obtain a user hash, at the first client device;

generating a second nonce corresponding to the user hash, at the core server;

transmitting the second nonce to the first client device from the core server;

concatenating the second nonce to the user hash to obtain a second resultant string, and applying the hashing algorithm to the second resultant string to obtain the identification hash, at the first client device.

3. The computer implemented method as claimed in claim 1, wherein the identification hash is sent to the API server through a first offline communication medium.

4. The computer implemented method as claimed in claim 3, wherein the first offline communication medium is selected from a group including Quick Response (QR) code, Near Field Communication (NFC) and Bluetooth.

5. The computer implemented method as claimed in claim 1, further comprising the step of displaying one or more first details corresponding to the user on the first client device to allow verification of an identity of the user.

6. The computer implemented method as claimed in claim 1, wherein the plurality of attributes comprise a geographical location tag and a time stamp.

7. The computer implemented method as claimed in claim 1, wherein the de-identified data, the record identification, the transaction identification, the record hash and the data hash is transmitted to the first client device in response to receiving of the identification hash from the first client device.

8. The computer implemented method as claimed in claim 1, further comprising the steps of:

regenerating the register package based on the identification hash, the record hash and the data hash at the first client device; and verifying the register package with the blockchain, by using the transaction identification, from the first client device.

9. The computer implemented method as claimed in claim 1, further comprising the step of verifying the de-identified data with the first client device, after transmitting the de-identified data to the first client device from the core server.

10. The computer implemented method as claimed in claim 1, further comprising the step of verifying the register package with the first client device before storing the register package onto the blockchain.

11. The computer implemented method as claimed in claim 1, further comprising the steps of:

regenerating the register package at the first client device based on the identification hash, the record hash and the data hash;

sending the record identification and a portion of the register package to a second client device, from the first client device;

sending the record identification and the portion of the register package to the core server for retrieval of the de-identified data, from the second client device;

querying the repository database from the core server using the record identification and the portion of the register package and receiving the transaction identification, the identification hash, the record hash, the data hash and the de-identified data at the core server from the repository database in response to the query; and sending, from the core server, at least one of the de-identified data and a first viewing medium to the second client device, the first viewing medium being configured for viewing of the de-identified data at the second client device.

12. The computer implemented method as claimed in claim 11, further comprising the steps of:

regenerating the register package at the core server based on the identification hash, the record hash and the data hash;

sending the register package and the transaction identification from the core server to the second client device; and verifying the register package with the blockchain using the transaction identification, from the second client device.

13. The computer implemented method as claimed in claim 11, further comprising the step of:

regenerating the register package at the core server based on the identification hash, the record hash and the data hash; and verifying the regenerated register package with the portion of the register package received from the second client device, at the core server.

14. The computer implemented method as claimed in claim 11, wherein the record identification and the portion of the register package are sent to the second client device through a second offline communication medium.

15. The computer implemented method as claimed in claim 14, wherein the second offline communication medium is selected from a group including Quick Response (QR) code, Near Field Communication (NFC) and Bluetooth.

16. The computer implemented method as claimed in claim 11, further comprising the step of sending one or more second details corresponding to the user by the first client device for verification of an identity of the user.

17. The computer implemented method as claimed in claim 1, further comprising the steps of:

regenerating the register package at the first client device based on the identification hash, the record hash and the data hash;

sending the register package and the transaction identification to a claims authorization server, from the first client device;

verifying the register package with the blockchain from the claims authorization server, using the transaction identification; and returning a confidence value from the claims authorization server to the first client device on verification of the register package.

18. The computer implemented method as claimed in claim 1, further comprising the steps of:

generating a research query at a third client device, the research query comprising a plurality of characteristics;

sending the research query to the core server from the third client device;

verifying from the core server, of a presence of at least one characteristic from the plurality of characteristics, in the de-identified data stored at the repository database;

requesting the first client device for an access to the de-identified data from the core server, on verification of the presence of the at least one characteristic;

receiving the record identification from the first client device in response to the request, at the core server and transmitting the record identification to a research database, from the core server;

generating a research record hash at the core server, and transmitting the research record hash to the research database to be stored in association with the record identification; and transmitting the research record hash to the third client device.

19. The method as claimed in claim 18, further comprising:

querying the core server using the research record hash for viewing of the de-identified data, from the third client device;

querying the research database from the core server using the research record hash and receiving the record identification at the core server from the research database;

querying the repository database from the core server using the record identification and receiving the de-identified data at the core server from the repository database; and sending, from the core server, a second viewing medium to the third client device, the second viewing medium being configured for viewing of the de-identified data at the third client device.

20. The computer implemented method as claimed in claim 18, wherein the first client device receives the request for access to the de-identified data on sending the identification hash to the core server.

21. A computer implemented method for secure management of data generated in an Electronic Health Record (EHR) during an episode of care, for a user, wherein the EHR is being maintained in a medical database comprised within a Healthcare Service Provider (HSP) server, the computer implemented method comprising the steps of:

sending an identification hash corresponding to the user to an Application Program Interface (API) server from a first client device;

extracting the data from the HSP server and de-identifying the data to obtain de-identified data, at the API server;

generating a record hash at the API server;

transmitting the identification hash, the record hash and the de-identified data from the API server to a core server;

receiving the identification hash, the record hash and the de-identified data at the core server and transmitting the identification hash, the record hash and the de-identified data from the core server to a repository database to generate a record identification;

transmitting the de-identified data, the record hash and the record identification from the repository database to the first client device, via the core server;

generating a data hash by hashing the de-identified data and a plurality of attributes corresponding to the de-identified data and generating a register package based on the identification hash, the record hash and the data hash, at the core server;

storing the register package, from the core server, on to a blockchain to generate a transaction identification;

transmitting the data hash and the transaction identification from the core server to the repository;

transmitting the transaction identification and the data hash to the first client device from the repository database, via the core server;

regenerating the register package at the first client device based on the identification hash, the record hash and the data hash; and verifying the register package with the blockchain by using the transaction identification, from the first client device.

22. A computer implemented method for facilitating secure management of data generated in an Electronic Health Record (EHR) during an episode of care, for a user, wherein the EHR is being maintained in a medical database comprised within a Healthcare Service Provider (HSP) server, the computer implemented method comprising the steps of:

regenerating a register package at a first client device based on an identification hash, a record hash and a data hash;

sending a record identification and a portion of the register package to a second client device, from the first client device;

sending the record identification and the portion of the register package to the core server for retrieval of de-identified data, from the second client device;

querying the repository database from the core server using the record identification and the portion of the register package and receiving a transaction identification, the identification hash, the record hash, the data hash and the de-identified data at the core server from the repository database in response to the query;

sending, from the core server, at least one of the de-identified data and a first viewing medium to the second client device, the first viewing medium being configured for viewing of the de-identified data at the second client device;

regenerating the register package at the core server based on the identification hash, the record hash and the data hash;

sending the register package and the transaction identification from the core server to the second client device; and verifying the register package with the blockchain using the transaction identification, from the second client device.

23. A computer implemented method for facilitating secure management of data generated in an Electronic Health Record (EHR) during an episode of care, for a user, wherein the EHR is being maintained in a medical database comprised within a Healthcare Service Provider (HSP) server, the computer implemented method comprising the steps of:

generating a research query at a third client device, the research query comprising a plurality of characteristics;

sending the research query to a core server from the third client device;

verifying from the core server, of a presence of at least one characteristic from the plurality of characteristics, in de-identified data stored at a repository database;

requesting the first client device for an access to the de-identified data from the core server, on verification of the presence of the at least one characteristic;

receiving the record identification from the first client device in response to the request, at the core server and transmitting the record identification to a research database, from the core server;

generating a research record hash at the core server, and transmitting the research record hash to the research database to be stored in association with the record identification;

transmitting the research record hash to the third client device querying the core server using the research record hash for viewing of the de-identified data, from the third client device;

querying the research database from the core server using the research record hash and receiving the record identification at the core server from the research database;

querying the repository database from the core server using the record identification and receiving the de-identified data at the core server from the repository database; and sending, from the core server, a second viewing medium to the third client device, the second viewing medium being configured for viewing of the de-identified data at the third client device.

24. A system for secure management of data generated in an Electronic Health Record (EHR), during an episode of care, for a user, wherein the EHR is being maintained in a medical database comprised within a Healthcare Service Provider (HSP) server, the system comprising:

an Application Program Interface (API) server operably connected to the HSP server through a network;

a core server operably connected to the API server through the network;

a first client device having a first memory and a first processor, the first memory being operably connected to the first processor and the first client device being operably connected to the API server and the core server through the network;

a repository database operably connected to the core server; and a blockchain operably connected to the network;

wherein the first memory is configured to store first computer program code, when executed by the first processor, enable the first processor to:
send an identification hash to the API server;
receive de-identified data, a record hash and a transaction identification from the repository database, via the core server; and
receive a transaction identification and a data hash from the repository database, via the core server;

wherein the API server is configured to:
receive the identification hash from the first client device;
generate a record hash;
extract the data from the HSP server and de-identify the data to obtain de-identified data;
transmit the identification hash, the record hash and the de-identified data to the core server;

wherein the core server is configured to:
receive the de-identified data, the identification hash and the record hash from the API server and transmit the de-identified data, the identification hash and the record hash to the repository database to generate the record identification;
transmit the de-identified data, the record hash and the record identification from the repository database to the first client device;
generate the data hash by hashing the de-identified data and a plurality of attributes corresponding to the de-identified data and generate a register package based on the data hash, the identification hash and the record hash;
store the register package on to the blockchain to generate the transaction identification;
transmit the data hash and the transaction identification to the repository database; and
transmit the transaction identification and the data hash from the repository database to the first client device.

25. The system as claimed in claim 24, wherein the first computer program code further enables the first processor to:
generate an asymmetrical pair of a public key and a private key;
concatenate a first nonce to the public key to obtain a first resultant string, and apply a hashing algorithm to the first resultant string to obtain a user hash; and
receive a second nonce from the core server; and
concatenate the second nonce to the user hash to generate a second resultant string and apply the hashing algorithm to the second resultant string to generate the identification hash;
wherein the core server is further configured to:
generate the second nonce corresponding to the user hash and transmit the second nonce to the first client device.

26. The system as claimed in claim 24, wherein the identification hash is sent to the API server through a first offline communication medium.

27. The system as claimed in claim 26, wherein the first offline communication medium is selected from a group including Quick Response (QR) code, Near Field Communication (NFC) and Bluetooth.

28. The system as claimed in claim 24, wherein the first computer program code further enables the first processor to display one or more first details corresponding to the user to allow verification of an identity of the user.

29. The system as claimed in claim 24, wherein the plurality of attributes comprise a geographical location tag and a time stamp.

30. The system as claimed in claim 24, wherein the first processor is enabled to receive the de-identified data, the record identification, the transaction identification, the record hash and the data hash from the core server in response to sending the identification hash to the core server.

31. The system as claimed in claim 24, wherein the first computer program code, further enables the first processor to:
regenerate the register package based on the identification hash, the record hash and the data hash; and
verify the register package with the blockchain by using the transaction identification.

32. The system as claimed in claim 24, wherein the core server is further configured to verify the de-identified data with the first client device after transmitting the de-identified data to the first client device.

33. The system as claimed in claim 24, wherein the core server is further configured to verify the register package with the first client device, before storing the register package on to the blockchain.

34. The system as claimed in claim 24, further comprising a second client device operably connected to the network, and having a second memory and a second processor, the second memory being operably connected to the second processor;

wherein the second memory is configured to store a second computer program code, the second program code when executed by the second processor, enable the second processor to:
  receive the record identification and a portion of the register package from the first client device;
  send the record identification and the portion of the register package to the core server for retrieval of the de-identified data; and
  receive, from the core server, at least one of the de-identified data and a first viewing medium at the second client device, the first viewing medium being configured for viewing of the de-identified data at the second client device;
wherein the first computer program code further enables the first processor to:
  regenerate the register package based on the identification hash, the record hash and the data hash; and
  send the record identification and the portion of the register package to the second client device;
wherein the core server is further configured to:
  receive the record identification and the portion of the register package from the second client device;
  query the repository database using the record identification and the portion of the register package and receive the transaction identification, the identification hash, the record hash, the data hash and the de-identified data from the repository database in response to the query; and
  send at least one of the de-identified data and the first viewing medium to the second client device.

35. The system as claimed in claim 34, wherein the second processor is further enabled to:
  receive the register package and the transaction identification from the core server; and
  verify the register package with the blockchain using the transaction identification;
wherein the core server is further configured to:
  regenerate the register package based on the identification hash, the record hash and the data hash; and
  transmit the register package and the transaction identification to the second client device.

36. The system as claimed in claim 34, wherein the core server is further configured to:
  regenerate the register package based on the identification hash, the record hash and the data hash; and
  verify the regenerated register package with the portion of the register package received from the second client device.

37. The system as claimed in claim 34, wherein the record identification and the portion of register package are sent to the second client device through a second offline communication medium.

38. The system as claimed in claim 37, wherein the second offline communication medium is selected from a group including Quick Response (QR) code, Near Field Communication (NFC) and Bluetooth.

39. The system as claimed in claim 34, wherein the first computer code further enables the first processor to send one or more second details corresponding to the user for verification of an identity of the user.

40. The system as claimed in claim 24, further comprising a claims authorization server;
wherein the first processor is further enabled to:
  regenerate the register package based on the identification hash, the record hash and the data hash to;
  send the register package and the transaction identification to the claims authorization server; and
  receive a confidence value from the claims authorization server;
wherein the claims authorization server is configured to:
  verify the register package with the blockchain, using the transaction identification; and
  return the confidence value to the first client device on verification of the register package.

41. The system as claimed in claim 24, further comprising:
  a research database operably connected to the network; and
  a third client device operably connected to the network, and having a third memory and a third processor, the third memory being operably connected to the third processor;
  wherein the third memory is configured to store a third computer program code, the third program code when executed by the third processor, enables the third processor to:
    generate a research query, the research query comprising a plurality of characteristics;
    send the research query to the core server; and
    receive a research record hash from the core server;
  wherein the core server is further configured to:
    verify a presence of at least one characteristic from the plurality of characteristics, in the de-identified data stored at the repository database;
    request the first client device for an access to the de-identified data, on verification of the presence of the at least one characteristic;
    receive the record identification from the first client device in response to the request and transmit the record identification to the research database;
    generate the research record hash and transmit the research record hash to the research database to be stored in association with the record identification; and
    transmit the research record hash to the third client device;
  wherein the first computer program code further enables the first processor to:
    receive the request for the access to the de-identified data; and
    transmit the record identification to the core server in response to the request.

42. The system as claimed in claim 41, wherein the third computer program code further enables the third processor to:
  query the core server using the research record hash for viewing of the de-identified data; and
  receive a second viewing medium at the third client device, in response to the query, the second viewing medium being configured for viewing of the de-identified data at the third client device;
wherein the core server is further configured to:
  receive the research record hash from the third client device; and
  query the research database using the research record hash and receive the record identification from the research database;
  query the repository database using the record identification and receive the de-identified data at the core server from the repository database; and
  send the second viewing medium to the third client device.

43. The system as claimed in claim 41, wherein the first processor is enabled to receive the request for access to the de-identified data on sending the identification hash to the core server.

44. A system for secure management of data generated in an Electronic Health Record (EHR) during an episode of care, for a user, wherein the EHR is being maintained in a medical database comprised within a Healthcare Service Provider (HSP) server, the system comprising:
an Application Program Interface (API) server operably connected to the HSP server;
a core server operably connected to the API server through a network;
a first client device having a first memory and a first processor and operably connected to the API server and the core server through the network;
a repository database operably connected to the core server; and
a blockchain operably connected to the network;
wherein the first memory is configured to store a first computer program code, when executed by the first processor, enable the first processor to:
send an identification hash to the API server;
receive de-identified data, a record hash and a transaction identification from the repository database, via the core server;
receive a transaction identification and a data hash from the repository database, via the core server;
regenerate a register package based on the identification hash, the record hash and the data hash; and
verify the register package with the blockchain by using the transaction identification;
wherein the API server is configured to:
receive the identification hash from the first client device;
extract the data from the HSP server and de-identify the data to obtain the de-identified data;
generate the record hash; and
transmit the identification hash, the record hash and the de-identified data to the core server;
wherein the core server is configured to:
receive the identification hash, the record hash and the de-identified data from the API server and transmit the identification hash, the record hash and the de-identified data to the repository database to generate the record identification;
transmit the de-identified data, the record hash and the record identification from the repository database to the first client device;
generate a data hash by hashing the de-identified data and a plurality of attributes corresponding to the de-identified data, and generate the register package based on the identification hash, the record hash and the data hash;
store the register package on to the blockchain to generate the transaction identification;
transmit the data hash and the transaction identification to the repository database; and
transmit the transaction identification and the data hash from the repository database to the first client device.

45. A core server for facilitating secure management of data generated in an Electronic Health Record (EHR), during an episode of care, for a user, wherein the EHR is being maintained in a medical database comprised within a Healthcare Service Provider (HSP) server, the core server configured to:

receive de-identified data, an identification hash and a record hash from an API server and transmit the identification hash, the record hash and the de-identified data to a repository database to generate a record identification;
transmit the de-identified, the record hash and the record identification from the repository database to a first client device;
generate a data hash by hashing the de-identified data and a plurality of attributes corresponding to the de-identified data and generate a register package based on the data hash, the identification hash and the record hash:
store the register package onto a blockchain to generate a transaction identification;
transmit the data hash and the transaction identification to a repository database; and
transmit the transaction identification and the data hash from the repository database to the first client device.

46. The core server as claimed in claim 45, further configured to:
generate a second nonce corresponding to a user hash and transmit the second nonce to the first client device.

47. The core server as claimed in claim 45, wherein the plurality of attributes comprise a geographical location tag and a time stamp.

48. The core server as claimed in claim 45, further configured to verify the de-identified data with the first client device after transmitting the de-identified data to the first client device.

49. The core server as claimed in claim 45, further configured to verify the register package with the first client device, before storing the register package on to the blockchain.

50. The core server as claimed in claim 45, further configured to:
receive the record identification and a portion of the register package for retrieval of the de-identified data, from a second client device;
query the repository database using the record identification and the portion of the register package and receive the transaction identification, the identification hash, the record hash, the data hash and the de-identified data from the repository database in response to the query; and
send at least one of the de-identified data and a first viewing medium to the second client device, the first viewing medium being configured for viewing of the de-identified data at the second client device.

51. The core server as claimed in claim 50, further configured to:
regenerate the register package based on the identification hash, the record hash and the data hash; and
send the register package and the transaction identification to the second client device.

52. The core server as claimed in claim 50, further configured to:
regenerate the register package based on the identification hash, the record hash and the data hash; and
verify the regenerated register package with the portion of the register package received from the second client device.

53. The core server as claimed in claim 45, further configured to:
receive a research query from a third client device, the research query comprising a plurality of characteristics;

verify a presence of at least one characteristic from the plurality of characteristics, in the de-identified data stored at the repository database;

request the first client device for an access to the de-identified data, on verification of the presence of the at least one characteristic;

receive the record identification from the first client device in response to the request and transmit the record identification to a research database;

generate a research record hash and transmit the research record hash to the research database to be stored in association with the record identification; and transmit the research record hash to the third client device.

54. The core server as claimed in claim 53, further configured to:

receive the research record hash from the third client device for viewing of the de-identified data;

query the research database using the research record hash and receive the record identification from the research database;

query the repository database using the record identification and receive the de-identified data at the core server from the repository database; and send a second viewing medium to the third client device, the second viewing medium being configured for viewing of the de-identified data at the third client device.

55. A second client device for facilitating secure management of data generated in an Electronic Health Record (EHR), during an episode of care, for a user, wherein the EHR is being maintained in a medical database comprised within a Healthcare Service Provider (HSP) server, the second client device comprising:

a second memory operably connected to a second processor, the second memory comprising a second computer program code stored thereon, the second program code when executed by the second processor, enables the second processor to:

receive a record identification and a portion of a register package from a first client device;

send the record identification and the portion of the register package to a core server for retrieval of de-identified data;

receive, from the core server, a viewing medium at the second client device, the viewing medium being configured for viewing of the de-identified data at the second client device;

receive the register package and a transaction identification from the core server; and verify the register package with the blockchain using the transaction identification.

56. A system for facilitating secure management of data generated in an Electronic Health Record (EHR) during an episode of care, for a user, wherein the EHR is being maintained in a medical database comprised within a Healthcare Service Provider (HSP) server, the system comprising:

a first client device having a first processor and a first memory, the first processor being operably connected to the first memory;

a claims authorization server operably connected to the first client device through a network;

wherein the first memory comprises a first computer program code, the first computer program code when executed by the first processor, enables the first processor to:

regenerate a register package based on an identification hash, a record hash and a data hash;

send the register package and a transaction identification to the claims authorization server; and receive a confidence value from the claims authorization server;

wherein the claims authorization server is configured to:

verify the register package with a blockchain, using the transaction identification; and return the confidence value to the first client device on verification of the register package.

57. A system for facilitating secure management of data generated in an Electronic Health Record (EHR) during an episode of care, for a user, wherein the EHR is being maintained in a medical database comprised within a Healthcare Service Provider (HSP) server, the system comprising:

a first client device having a first processor and a first memory, the first processor being operably connected to the first memory;

a third client device having a third processor and a third memory, the third processor being operably connected to the third memory;

a core server operably connected to the third client device through a network;

a repository database operably connected to the core server; and a research database operably connected to the network;

wherein the third memory comprises a third computer program code, the third computer program code when executed by the third processor, enables the third processor to:

generate a research query, the research query comprising a plurality of characteristics;

send the research query to the core server;

receive a research record hash from the core server;

query the core server using the research record hash for viewing of the de-identified data; and receive a second viewing medium at the third client device, in response to the query, the second viewing medium being configured for viewing of the de-identified data at the third client device;

wherein the core server is configured to:

verify a presence of at least one characteristic from the plurality of characteristics, in the de-identified data stored at the repository database;

request the first client device for an access to the de-identified data, on verification of the presence of the at least one characteristic;

receive the record identification from the first client device in response to the request and transmit the record identification to the research database;

generate the research record hash and transmit the research record hash to the research database to be stored in association with the record identification;

transmit the research record hash to the third client device;

receive the research record hash from the third client device;

query the research database using the research record hash and receive the record identification from the research database;

query the repository database using the record identification and receive the de-identified data at the core server from the repository database; and send the second viewing medium to the third client device;

wherein the first memory comprises a first computer program code, the first computer program code when executed by the first processor, enables the first processor to:

receive the request for the access to the de-identified data; and transmit the record identification to the core server in response to the request.

58. The system as claimed in claim 57, wherein the first processor is enabled to receive the request for access to the de-identified data on sending an identification hash to the core server.

* * * * *